(12) United States Patent
Mori et al.

(10) Patent No.: US 10,874,374 B2
(45) Date of Patent: Dec. 29, 2020

(54) MEDICAL IMAGE-PROCESSING APPARATUS AND ULTRASONIC DIAGNOSTIC DEVICE

(71) Applicant: Toshiba Medical Systems Corporation, Otawara (JP)

(72) Inventors: Kei Mori, Shioyagun (JP); Atsuko Sugiyama, Nasushiobara (JP); Mariko Shibata, Nasushiobara (JP); Yoshimasa Kobayashi, Nasushiobara (JP); Toshie Maruyama, Yaita (JP); Koichi Terai, Shioyagun (JP); Natsuki Sato, Kashiwa (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 920 days.

(21) Appl. No.: 15/339,084

(22) Filed: Oct. 31, 2016

(65) Prior Publication Data

US 2017/0128037 A1  May 11, 2017

(30) Foreign Application Priority Data

Nov. 11, 2015  (JP) .................................. 2015-221558

(51) Int. Cl.
*A61B 8/00* (2006.01)
*A61B 8/08* (2006.01)
(Continued)

(52) U.S. Cl.
CPC ............ *A61B 8/0825* (2013.01); *A61B 6/463* (2013.01); *A61B 6/469* (2013.01); *A61B 6/502* (2013.01);
(Continued)

(58) Field of Classification Search
CPC ..... A61B 8/0825; A61B 6/5217; A61B 6/502; A61B 8/14; A61B 8/469; A61B 8/463; A61B 6/469; A61B 6/463
See application file for complete search history.

(56) References Cited

U.S. PATENT DOCUMENTS

| | | | |
|---|---|---|---|
| 2009/0118614 | A1 | 5/2009 | Sendai |
| 2014/0135623 | A1 | 5/2014 | Manak |
| 2016/0110875 | A1 | 4/2016 | Sugiyama et al. |

FOREIGN PATENT DOCUMENTS

| | | |
|---|---|---|
| JP | 2005-125080 A | 5/2005 |
| JP | 2008/154833 | 7/2008 |

(Continued)

OTHER PUBLICATIONS

Japanese Office Action dated Sep. 8, 2020, issued in Japanese Patent Application No. 2016-206285.

*Primary Examiner* — Joel Lamprecht
(74) *Attorney, Agent, or Firm* — Oblon, McClelland, Maier & Neustadt, L.L.P.

(57) ABSTRACT

A medical image processing apparatus of an embodiment includes storage circuitry and setting-condition determining circuitry. The storage circuitry stores information about at least one of a position of a region of interest in a breast, a size of the region of interest, and a size of the breast, the information acquired based on an X-ray image of a breast of a subject. The setting-condition determining circuitry acquires a setting condition in ultrasonographic diagnosis for the breast based on the information about at least one of the position of the region of interest, the size of the region of interest, and the size of the breast.

16 Claims, 15 Drawing Sheets

(51) Int. Cl.
*A61B 6/00* (2006.01)
*A61B 8/14* (2006.01)

(52) U.S. Cl.
CPC ............ *A61B 6/5217* (2013.01); *A61B 8/463* (2013.01); *A61B 8/469* (2013.01); *A61B 8/14* (2013.01)

(56) References Cited

FOREIGN PATENT DOCUMENTS

| | | |
|---|---|---|
| JP | 2008-161283 | 7/2008 |
| JP | 2008-206747 A | 9/2008 |
| JP | 2009-72410 | 4/2009 |
| JP | 2009-172226 A | 8/2009 |
| JP | 2013-094538 A | 5/2013 |
| JP | 2014-014489 A | 1/2014 |
| JP | 2015-27450 | 2/2015 |
| JP | 2015-167829 A | 9/2015 |
| WO | WO-2015002256 A1 * | 1/2015 |

* cited by examiner

FIG.11
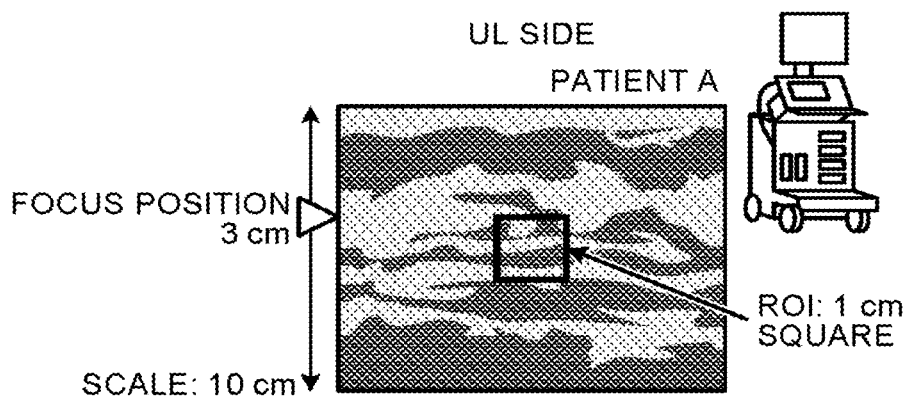
FIG.12
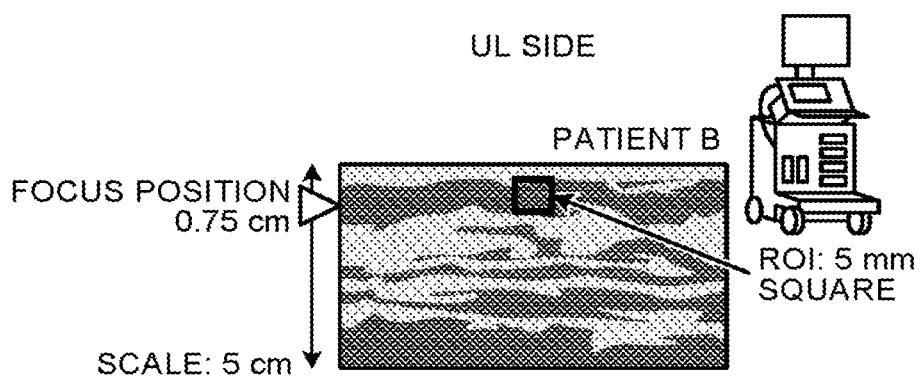
FIG.13
| BREAST REGION INFORMATION (SIZE OF BREAST) | DEFAULT SETTING | SETTING AFTER CHANGE |
|---|---|---|
| LARGE | 8 cm | 10 cm |
| MIDDLE | 8 cm | NOT CHANGED |
| SMALL | 8 cm | 5 cm |

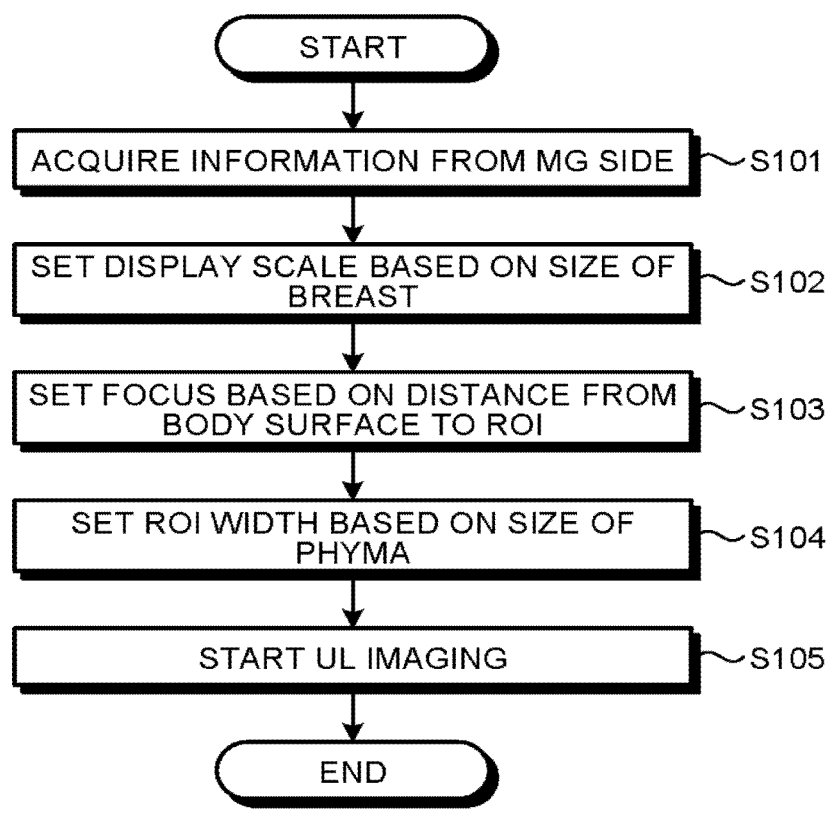

| SCHEMATIC DIAGRAM | BODY MARK |
|---|---|
| RIGHT BREAST SCHEMATIC DIAGRAM | #1 |
| LEFT BREAST SCHEMATIC DIAGRAM | #2 |

MEDICAL IMAGE-PROCESSING APPARATUS AND ULTRASONIC DIAGNOSTIC DEVICE

CROSS-REFERENCE TO RELATED APPLICATIONS

This application is based upon and claims the benefit of priority from Japanese Patent Application No. 2015-221558, filed on Nov. 11, 2015; the entire contents of which are incorporated herein by reference.

FIELD

Embodiments described herein relate generally to a medical image-processing apparatus and ultrasonic diagnostic device.

BACKGROUND

Triggered by the start of a project called Japan Strategic Anti-cancer Randomized Trial (J-START), examinations using both mammographic images and ultrasonic images (hereinafter, "MG-UL examination") are expected to be prevailed. In the MG-UL examination, improvement in workflow is desired since an operation of acquiring ultrasonic images is added in the MG-UL examination compared to an examination by mammographic images.

BRIEF DESCRIPTION OF THE DRAWINGS

FIG. 11 is a diagram (1) for explaining the first embodiment;

FIG. 12 is a diagram (2) for explaining the first embodiment;

FIG. 13 is a diagram (3) for explaining the first embodiment;

FIG. 14 is a diagram (4) for explaining the first embodiment;

FIG. 15 is a flowchart of a processing procedure of the ultrasonic diagnostic device according to the first embodiment;

DETAILED DESCRIPTION

A medical image-processing apparatus and an ultrasonic diagnostic device according to embodiments are explained below with reference to drawings. Embodiments are not limited to the embodiments below. Moreover, what is described in one embodiment is basically applied similarly to other embodiments.

The medical image-processing apparatus the embodiments includes storage circuitry and setting-condition determining circuitry. The storage circuitry stores information that is acquired based on an X-ray image a breast of a subject about at least one of a position of a region of interest in the breast, a size of the region of interest, and a size of the breast. The setting-condition determining circuitry acquires setting conditions in ultrasonographic diagnosis for the breast based on the information about at least one of the position of the region of interest, the size of the region of interest, and the size of the breast.

First Embodiment

Figure 1:
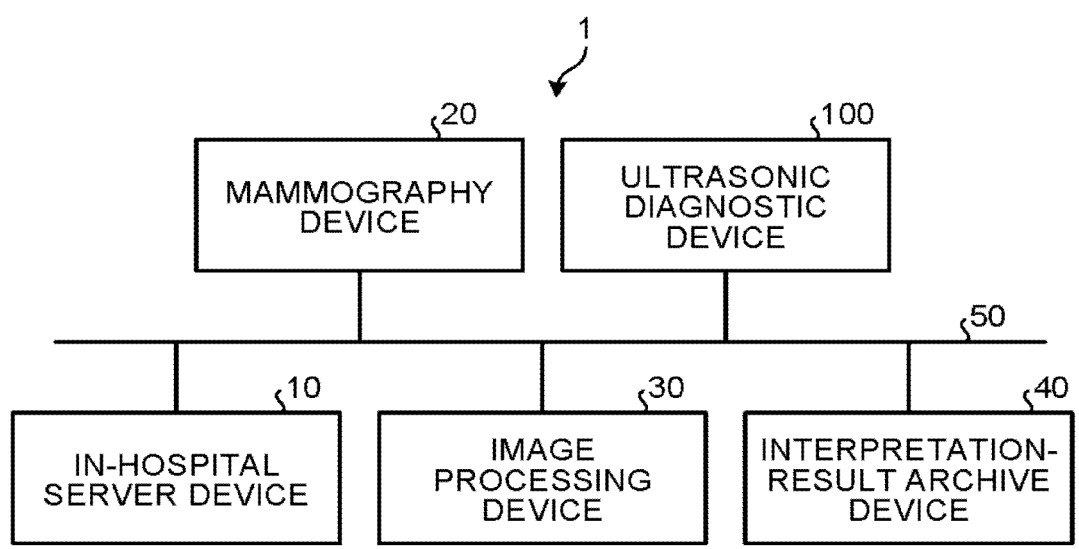
FIG. 1 depicts a configuration example of a medical information-processing system according to a first embodiment.

FIG. 1 depicts a configuration example of a medical information-processing system according to a first embodiment. The medical information-processing system according to the present embodiment is installed in a facility in which breast cancer examinations are held, and is used for mammographic diagnosis using both mammographic images and ultrasonic images. For example, as shown in FIG. 1, a medical information-processing system 1 according to the present embodiment includes an in-hospital server device 10, a mammography device 20, an image processing device 30, an interpretation-result archive device 40, and an ultrasonic diagnostic device 100. The respective devices are connected to each other through a network 50, and mutually communicate images obtained by the mammography device 20 or the ultrasonic diagnostic device 100, and the like.

The in-hospital server device 10 manages a medical information system. The medical information system is an information system that is used in a hospital, and is, for example, an electronic medical chart system, a medical-insurance computing system, an ordering system, a reception (personal, qualification authentication) system, a diagnosis supporting system, and the like. As one example, the in-hospital server device 10 accepts an appointment for a medical examination. For example, the in-hospital server device 10 accepts an input of patient information of a patient that is to have the medical examination, an examination type, and the like. The in-hospital server device 10 then registers an examination appointment in devices that are used for respective examinations. Thus, the examination for which the appointment has been made is conducted in the mammography device 20 or the ultrasonic diagnostic device 100.

The mammography device 20 irradiates an X-ray to a breast of a subject, and generates a mammographic image by detecting the X-ray that penetrates through the breast.

The image processing device 30 processes the mammographic image generated by the mammography device 20, and an ultrasonic image that is generated by the ultrasonic diagnostic device 100. This image processing device 30 is mainly used when a mammography examination is conducted by a technician of mammography examinations. Moreover, the image processing device 30 accepts an input of findings of the mammographic image from the technician of mammography examinations, and stores information indicating the accepted findings as finding information. For example, the image processing device 30 is an image archive server, a workstation, or the like, and is one example of a medical image-processing apparatus.

Figure 2:
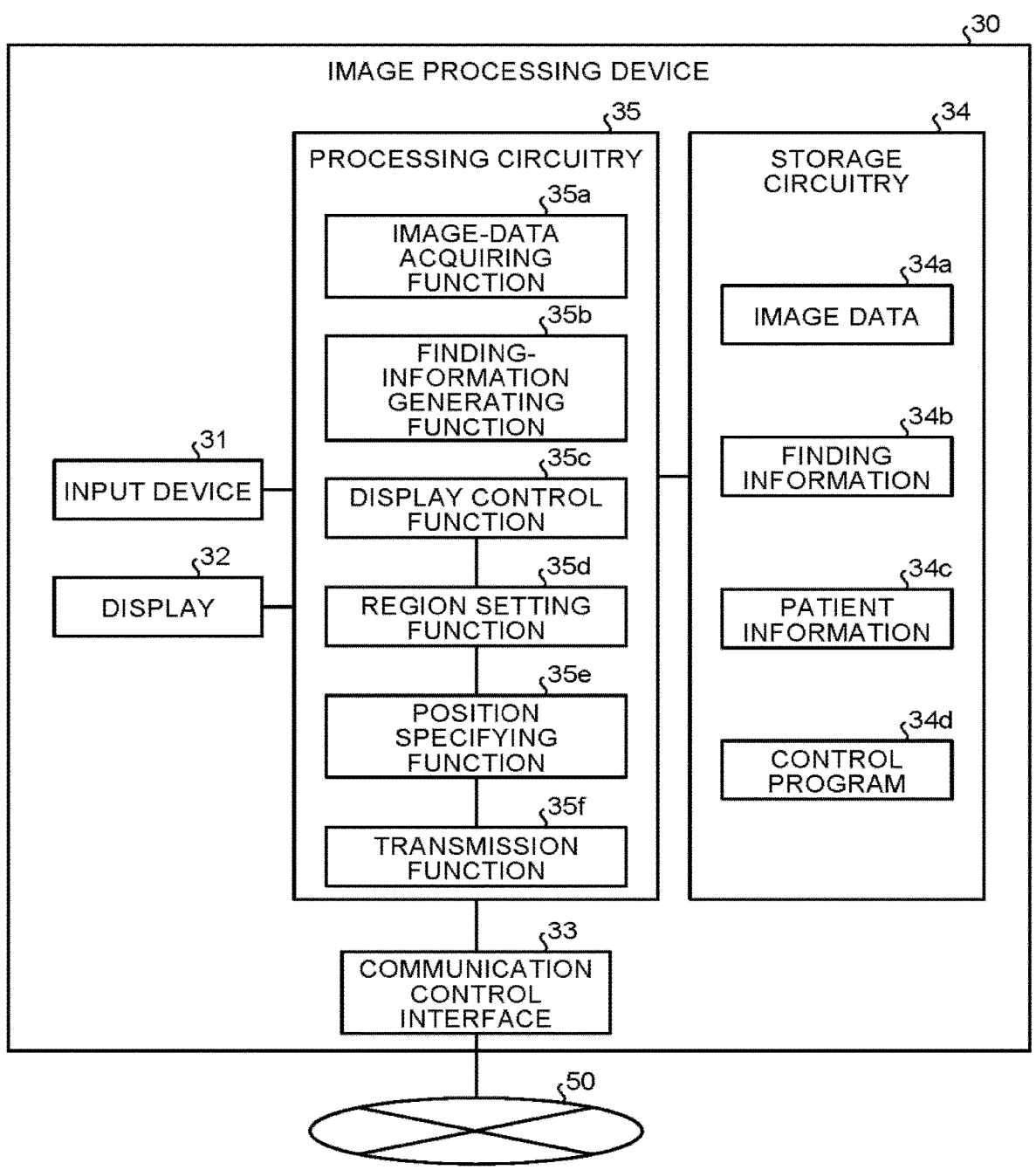
FIG. 2 depicts a configuration example of an image processing device according to a first embodiment.

FIG. 2 depicts a configuration example of the image processing device 30 according to the first embodiment. As shown in FIG. 2, the image processing device 30 includes an input device 31, a display 32, a communication control interface 33, storage circuitry 34, and processing circuitry 35.

The input device 31 accepts an input of various kinds of operations and various kinds of information from an operator. For example, the input device 31 is a keyboard, a mouse, button, a trackball, a touch panel, and the like.

The display 32 displays a graphical user interface (GUI) to accept various kinds of operations from an operator, and various kinds of images. For example, the display 32 is a liquid crystal display, a cathode ray tube (CRT) display, a touch panel, and the like.

The communication control interface 33 controls communication performed with other devices through the network 50. For example, the communication control interface 33 is a network card or a network adopter, and performs communication with other devices by connecting to the network 50 through an Ethernet (registered trademark) local area network (LAN). Furthermore, for example, the communication control interface 33 performs wireless communication with other devices by connecting to the network 50 through a wireless LAN.

The storage circuitry 34 is a storage device that stores various kinds of data, such as image data 34a, finding information 34b, and patient information 34c, and a control program 34d to perform image processing and display processing. Moreover, data stored in the storage circuitry 34 can be transferred to an external device through an interface not shown.

Various kinds of data stored in the storage circuitry 34 is explained. For example, the storage circuitry 34 stores a mammographic image that is obtained by imaging a breast of a subject, and information that indicates an imaging direction of the mammographic image. Specifically, the storage circuitry 34 stores the mammographic image and the information indicating the imaging direction associating with each other per image. The mammographic image and information indicating an imaging direction are stored by an image-data acquiring function 35a described later into the storage circuitry 34.

More specifically, the storage circuitry 34 stores a mammographic image of an MLO direction (MLO image) and mammographic image of a CC direction (CC image). Furthermore, the information indicating an imaging direction herein is position information that is expressed by a device coordinate system of the mammography device, and is added to each image when a mammographic image is generated by the mammography device as supplementary information.

Moreover, for example, the storage circuitry 34 stores the finding information 34b for a mammographic image of a subject. The finding information is stored by a finding-information generating function 35b described later into the storage circuitry 34. As one example, the storage circuitry 34 stores information in which "breast region information (size of breast)", "distance from body surface to ROI", and "size/shape of phyma" are associated with each other, as the finding information 34b.

Figure 3:
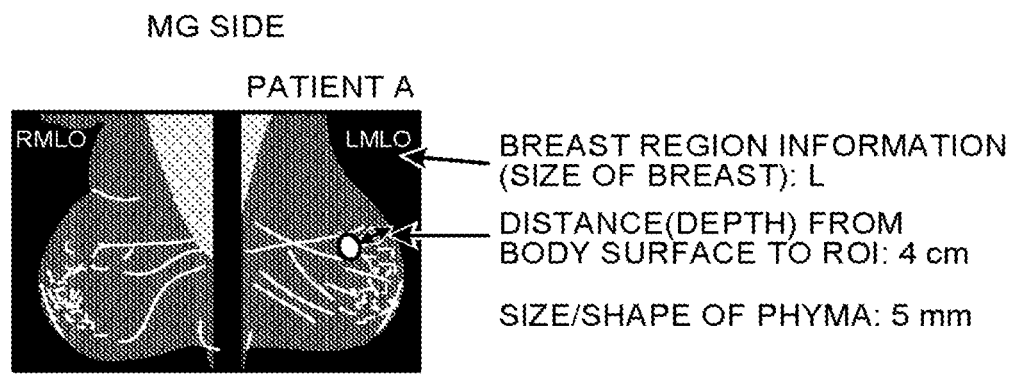
FIG. 3 is a diagram (1) for explaining finding information according to the first embodiment.
Figure 4:
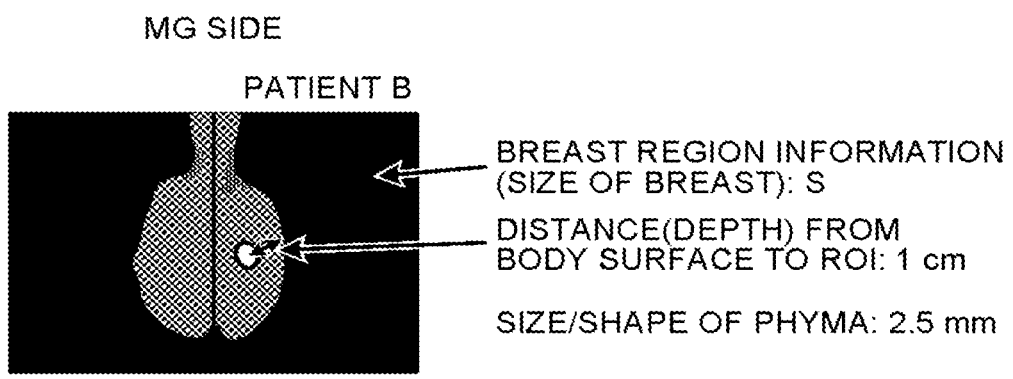
FIG. 4 is a diagram (2) for explaining finding information according to the first embodiment.

The finding information 34b is explained using FIG. 3 and FIG. 4. FIG. 3 and FIG. 4 are diagrams for explaining the finding information 34b according to the first embodiment. In FIG. 3, the finding information 34b of a patient A is explained, and in FIG. 4, the finding information 34b of a patient B is explained.

The "breast region information" stored as the finding information 34b indicates the size of a breast. For example, a value of "L", "M", "S", or the like is stored as the "breast region information". In the example shown in FIG. 3, the "breast region information" is "L", and in the example shown in FIG. 4, the "breast region information" is "S".

Furthermore, the "distance from body surface to ROI" that is stored as the finding information 34b indicates a distance between a region of interest (ROI) set in a mammographic image and a body surface in the mammographic image. In the example shown in FIG. 3, the "distance from body surface to ROI" is "4 cm", and in the example shown in FIG. 4, the "distance from body surface to ROI" is "1 cm". ROI is set by a region setting function 35d described later.

Moreover, the "size/shape of phyma" stored as the finding information 34b indicates the size or the shape of a candidate region of a lesion detected in a mammographic image. In the example shown in FIG. 3, the "size/shape of phyma" is "5 mm", and in the example shown in FIG. 4, the "size/shape of phyma" is "2.5 mm". ROI is set by the region setting function 35d described later. The size of phyma is set by the region setting function 35d, for example, by using a function of the finding-information generating function 35b described later or a computer aided diagnosis (CAD). As the finding information 34b, a distance from a nipple to a region of interest, such as a phyma, may be stored.

Furthermore, for example, the storage circuitry 34 stores the patient information 34c that enables to identify a patient uniquely. For example, the patient information includes a patient identifier (ID), name, age, consultation history, and the like.

The processing circuitry 35 controls operation of the image processing device 30. The processing circuitry 35 operates, as shown in FIG. 2, the image-data acquiring function 35a, the finding-information generating function 35b, a display control function 35c, the region setting function 35d, a position specifying function 35e, and a transmission function 35f. For example, respective processing functions performed by the image-data acquiring function 35a, the finding-information generating function 35b, the display control function 35c, the region setting function 35d, and the position specifying function 35e, and the transmission function 35f, which are components of the processing circuitry 35 shown in FIG. 2 are recorded in the storage circuitry 34 in a form of programs that can be executed by a computer. The processing circuitry 35 is a processor that implements the functions corresponding to the respective programs by reading and executing the respective programs from the storage circuitry 34. In other words, the processing circuitry 35 that has read the respective programs are to have the respective functions indicated in the processing circuitry 35 in FIG. 2.

The image-data acquiring function 35a acquires a mammographic image that is obtained by imaging a breast of a subject, and information indicating an imaging direction of the mammographic image. The image-data acquiring function acquires an MLO image and a CC image for each of right and left breasts of the subject. Specifically, the image-data acquiring function 35a acquires the mammographic image of a subject of diagnosis and the information indicating an imaging direction of the mammographic image by communication with the mammography device 20 through the communication control interface 33, and stores the acquired mammographic image and the information indicating an imaging direction in the storage circuitry 34. The image-data acquiring function 35a can acquire the mammographic image and the information indicating an imaging direction by a method other than the communication through the communication control interface 33. For example, when a mammographic image and information indicating an imaging direction of the mammographic image are recorded in a computer-readable recording medium, the image-data acquiring function 35a can acquire the mammographic image and the information indicating an imaging direction of the mammographic image from this recording medium. The computer-readable recording medium is, for example, a hard disk, a flexible disk (FD), a compact disc read-only memory (CD-ROM), a magneto-optical disk (MO), a digital versatile disc (DVD), a universal serial bus (USB) memory, and the like.

The finding-information generating function 35b generates finding information of a mammographic image of subject based on findings input by an operator. Specifically, the finding-information generating function 35b accepts an input of findings of a mammographic image from a technician of mammography examinations through the input device 31. The finding-information generating function 35b then generates finding information that indicates the accepted findings. For example, the finding-information generating function 35b generates finding information shown in FIG. 3 and FIG. 4. The finding-information generating function 35b stores the generated finding information in the storage circuitry 34.

The display control function 35c displays a reference screen to refer to a mammographic image on the display 32. Specifically, when accepting a display request from an operator through the input device 31, the display control function 35c reads a mammographic image of a subject of diagnosis from the storage circuitry 34, and reads the finding information 34b of the subject of diagnosis from the storage circuitry 34. The display control function 35c then displays a reference screen in which the read mammographic image and the finding information are arranged on the display 32.

The region setting function 35d sets a region of interest in a mammographic image. For example, the region setting function 35d sets a region of interest in each of the MLO image and the CC image of each of right and left breast of a subject. Specifically, the region setting function 35d accepts, through the input device 31, an operation of specifying a range of an arbitrary size at an arbitrary position on the mammographic image arranged in the reference screen displayed by the display control function 35c. The region setting function 35d then sets the range specified by the operator as a region of interest.

For example, the region setting function 35d can automatically detect a lesion candidate region from a mammographic image, and set the detected region as a region of interest by using a function of a computer-aided diagnosis. Moreover, for example, the region setting function 35d can accept an operation of adjusting a region detected by CAD between the MLO image and the CC image by an operator, and set the adjusted region as a region of interest.

The position specifying function 35e specifies position information of a region of interest on a schematic image that schematically expresses a breast based on position information of a region of interest on a mammographic image and information indicating an imaging direction. Specifically, the position specifying function 35e reads mammographic image of a subject of diagnosis and information indicating an imaging direction of the mammographic image from the storage circuitry 34, and specifies a position of a region of interest on a schematic diagram based on the read mammographic image and the information indicating an imaging direction.

Figure 5:
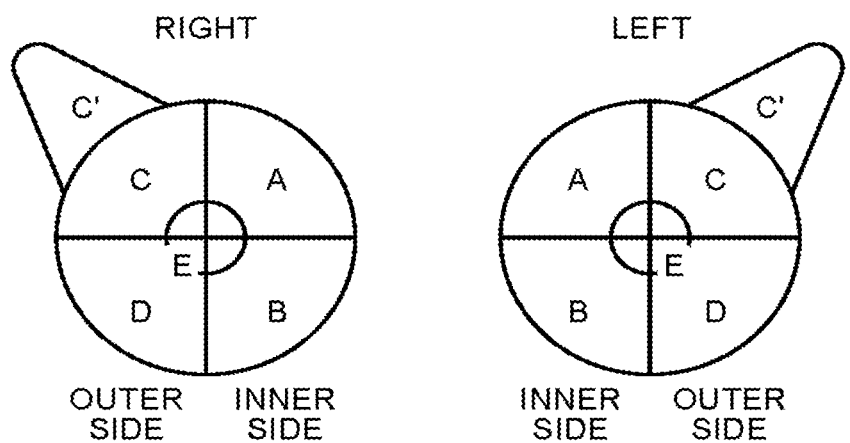
FIG. 5 depicts one example of a schematic diagram that is used by a position specifying function according to the first embodiment.

FIG. 5 depicts one example of the schematic diagram that is used by the position specifying function 35e according to the first embodiment. The example shown in FIG. 5 shows schematic diagram of a breast region as an example of the schematic diagram that schematically expresses breasts. For example, as shown in FIG. 5, the schematic diagram of a breast region has a circular region expressing a region of a breast (hereinafter, breast region) and a substantially triangular region expressing a region at an armpit (hereinafter, armpit region).

The circular region expressing a breast region is sectioned into upper, lower, left, and right parts, to be divided into four regions "A" to "D". For example, the of "A" (hereinafter, region A) indicates a region at an inner upper part of a breast, and the region of "B" (hereinafter, region B) indicates a region at an inner lower part of a breast. Furthermore, for example, the region of "C" (hereinafter, region C) indicates a region at an outer upper part of a breast, and the region of "D" (hereinafter, region D) indicates a region at an outer lower part of a breast. Moreover, the substantially triangular region of "C'" (hereinafter, region C') expressing an armpit region has shape extending diagonally upward from the region C, and becoming narrower as it becomes further away from the region C. Furthermore, for example, the region of "E" (hereinafter, region E) indicates an areola portion. As the schematic diagrams herein, various kinds of diagrams can be used as long as positional relationship in breasts are indicated.

The position specifying function 35e generates a schematic diagram to be archived in which a mark indicating a region of interest is positioned on a template of the schematic diagram of a breast region based on position information of each region on the schematic diagram. The schematic diagram to be archived is generated as image data in a format of, for example, joint photographic experts group (JPEG), graphics interchange format (GIF), bitmap, and the like.

Figure 6:
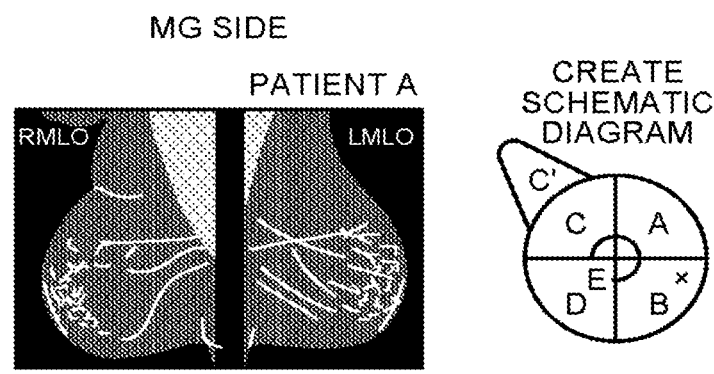
FIG. 6 is a diagram (1) for explaining a schematic diagram to be archived according to the first embodiment.
Figure 7:
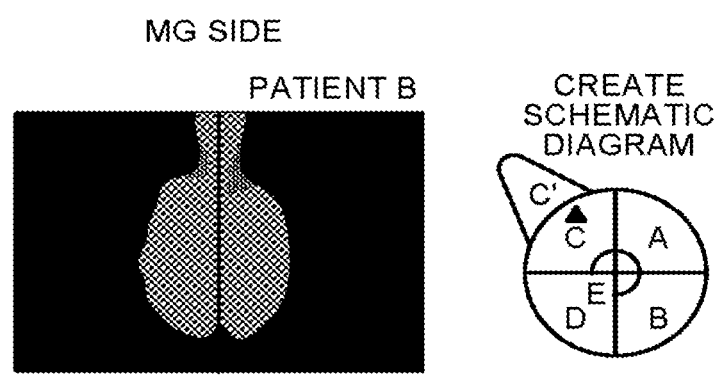
FIG. 7 is a diagram (2) for explaining a schematic diagram to be archived according to the first embodiment.

The schematic diagram to be archived is explained using FIG. 6 and FIG. 7. FIG. 6 and FIG. 7 are diagrams for explaining the schematic diagram to be archived according to the first embodiment. A left drawing in FIG. 6 shows a mammographic image of a patient A, and a right drawing in FIG. 6 shows a schematic diagram to be archived of the patient A. Similarly, a left drawing in FIG. 7 shows a mammographic image of a patient B, and a right drawing in FIG. 7 shows a schematic diagram to be archived of the patient B.

The position specifying function 35e generates a schematic diagram to be archived as shown in the right drawing in FIG. 6 when a region of interest is set in the region B of the right breast of the patient A. Moreover, the position specifying function 35e generates a schematic diagram to be archived as shown in the right drawing in FIG. 7 when a region of interest is set in the region C of the right breast of the patient B.

The position specifying function 35e then stores the generated schematic diagram to be archived, associating with a corresponding mammographic image in the storage circuitry 34. For example, the position specifying function 35e adds the generated schematic diagram to be archived to the mammographic image as supplementary information, and stores it together with image data of the mammographic image in the storage circuitry 34. Alternatively, the position specifying function 35e associates the generated schematic diagram to be archived with a patient ID that is assigned to the subject to be stored in the storage circuitry 34.

For example, when generating a schematic diagram to be archived by using a template of a schematic diagram, not just indicating position information of a region of interest on the schematic diagram, the position specifying function 35e can extract a region having a mammary density higher than a threshold, or a calcified region, a region of tumor, and the like from a mammographic image to display on the schematic diagram. For example, the position specifying function 35e shows portions corresponding to those regions on the schematic diagram in a different color from a color of the schematic diagram per type of the regions, or displays a mark predetermined per type of the regions.

Referring back to FIG. 2, the transmission function 35f transmits the finding information 34b generated by the finding-information generating function 35b or the schematic diagram to be archived generated by the position specifying function 35e to the interpretation-result archive device 40 or the ultrasonic diagnostic device 100 according to an instruction from an operator. Specifically, the transmission function 35f accepts a transmission instruction of display information from an operator of the image processing device 30 or the ultrasonic diagnostic device 100 through the input device 31. Accepting the transmission instruction of display information, the transmission function 35f reads display information specified by the operator from the storage circuitry 34, and transmits it to the interpretation-result archive device 40 or the ultrasonic diagnostic device 100.

The function can be implemented by integrating multiple components shown in FIG. 2 into a single processor. The word "processor" used in the above explanation signifies a circuit such as a central processing unit (CPU), a graphics processing unit (GPU), an application specified integrated circuit (ASIC), a programmable logic device (for example, simple programmable logic device (SPLD)), a complex programmable logic device (CPULD), and a field programmable gate array (FPGA). The processor implements the function by reading and executing a program stored in the storage circuitry 34. The program can be directly installed in the circuit instead of storing the program in the storage circuitry 34. In this case, the processor implements the function by reading and executing the program installed in the circuit. Each processor in the present embodiment is not limited to be configured with a single circuit per processor, but can also be configured as a single processor by combining multiple independent circuits to implement the function.

Referring back to FIG. 1, the interpretation-result archive device 40 stores an interpretation result for an image obtained in the medical information-processing system 1. For example, the interpretation-result archive device 40 stores the finding information 34b, which is a result of interpretation of a mammographic image, and the schematic diagram to be archived, and a result of interpretation of an ultrasonic image.

The ultrasonic diagnostic device 100 generates an ultrasonic image based on reflected waves that are collected by scanning a subject with an ultrasonic probe that transmits and receives ultrasonic waves.

Figure 8:
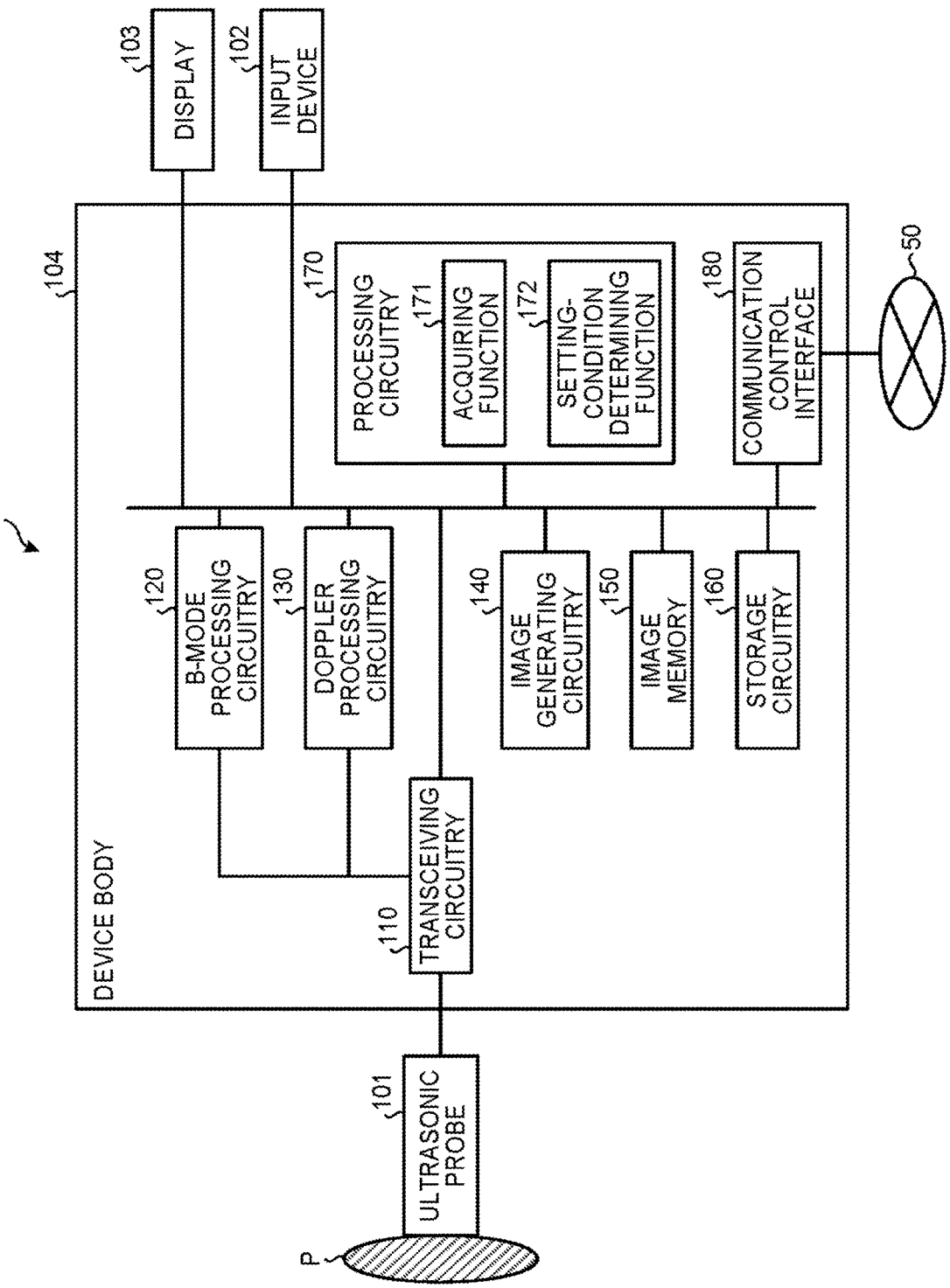
FIG. 8 depicts a configuration example of an ultrasonic diagnostic device according to the first embodiment.

FIG. 8 depicts a configuration example of the ultrasonic diagnostic device 100 according to the first embodiment. As shown in FIG. 8, the ultrasonic diagnostic device 100 according to the first embodiment includes an ultrasonic probe 101, an input device 102, a display 103, and a device body 104. The ultrasonic probe 101 is connected to transceiving circuitry 110 included in the device body 104 described later so as to be able to communicate therewith. Moreover, the input device 102 and the display 103 are connected to various kinds of circuits in the device body 104 so as to be able to communicate with each other.

The ultrasonic probe 101 is brought into contact with a body surface of a subject P, and transmits and receives ultrasonic waves. For example, the ultrasonic probe 101 has multiple piezoelectric resonators (also referred to as resonators). These piezoelectric resonators generate ultrasonic waves based on a transmission signal provided by the transceiving circuitry 110. The generated ultrasonic waves are reflected by body tissues of the subject P, and received by the piezoelectric resonators as a reflected wave signal. The ultrasonic probe 101 transmits the reflected wave signal received by the piezoelectric resonators to the transceiving circuitry 110.

The first embodiment is applicable when the ultrasonic probe 101 is either a 1-D array probe that scans a two-dimensional area (two-dimensional scanning) in the subject P, or a mechanical 4-D probe or 2-D array probe that scans a three-dimensional area (three-dimensional scanning) in the subject P.

The input device 102 corresponds to, for example, a mouse, a keyboard, a button, a panel switch, a touch command screen, a foot switch, a trackball, a joystick, and the like. The input device 102 accepts various kinds of setting requests from an operator of the ultrasonic diagnostic device 100, and transfers the accepted various kinds of setting requests to respective circuits of the device body 104 appropriately.

The display 103 displays a GUI for an operator to input various kinds of setting requests by using the input device 102, or displays an image (ultrasonic image) based on ultrasonic image data generated in the device body 104, and the like.

The device body 104 is a device that generates ultrasonic image data based on a reflected wave signal that is received by the ultrasonic probe 101. As shown in FIG. 8, the device body 104 includes, for example, the transceiving circuitry 110, B-mode processing circuitry 120, Doppler processing circuitry 130, image generating circuitry 140, an image memory 150, storage circuitry 160, processing circuitry 170, and a communication control interface 180. The transceiving circuitry 110, the B-mode processing circuitry 120, the Doppler processing circuitry 130, the image generating circuitry 140, the image memory 150, the storage circuitry 160, the processing circuitry 170, and the communication control interface 180 are connected to each other so as to enable mutual communication.

The transceiving circuitry 110 controls transmission and reception of ultrasonic waves by the ultrasonic probe 101. For example, the transceiving circuitry 110 controls transmission and reception of ultrasonic waves performed by the ultrasonic probe 101 based on an instruction of the processing circuitry 170 described later. The transceiving circuitry 110 generates transmission waveform data, and generates a transmission signal for the ultrasonic probe 101 to transmit an ultrasonic wave from the generated transmission waveform data. The transceiving circuitry 110 applies the transmission signal to the ultrasonic probe 101 thereby causing the ultrasonic probe 101 to transmit an ultrasonic beam in which ultrasonic waves converge into a beam form.

Furthermore, the transceiving circuitry 110 generates reflected wave data in which a reflection component from a direction according to a reception directivity of the reflected wave signal is emphasized by performing addition processing adding a predetermined delay time to the reflected wave signal that is received by the ultrasonic probe 101, and transmits the generated reflected wave data to the B-mode processing circuitry 120 and the Doppler processing circuitry 130.

For example, the transceiving circuitry 110 includes amplifier circuitry (hereinafter, "Amp" as appropriate), an analog/digital (A/D) converter (hereinafter, "ADC" as appropriate), generating circuitry, quadrature detection circuitry (hereinafter "IQ" as appropriate), and the like. The amplifier circuitry performs gain correction processing by amplifying the reflected wave signal per channel. The A/D converter performs A/D conversion of the reflected wave signal subjected to the gain correction.

The generating circuitry gives a reception delay time that is necessary for determining the reception directivity to digital data. The generating circuitry then performs addition processing of the reflected wave signal to which the reception delay time has been given. By the addition processing by the generating circuitry, a reflection component from a direction according to a reception directivity of the reflected wave signal is emphasized.

The quadrature detection circuitry converts an output signal of an adder into an in-phase signal (I signal) and a quadrature-phase signal (Q signal) of a baseband. The quadrature detection circuitry then stores the I signal and the Q signal (hereinafter, IQ signal) in a buffer as reflected wave data. The quadrature detection circuitry can convert the output signal of the adder into a radio frequency (RF) signal to store in the buffer. The IQ signal and the RF signal are to be a signal (reception signal) including phase information. Although it has been explained that the quadrature detection circuitry is arranged in a subsequent stage of the generating circuitry, embodiments are not limited thereto. For example, the quadrature detection circuitry can be arranged in a preceding stage of the generating circuitry. In this case, the generating circuitry performs the addition processing of the I signal and the Q signal.

The B-mode processing circuitry 120 performs various kinds of signal processing for the reflected wave data generated from the reflected wave signal by the transceiving circuitry 110. The B-mode processing circuitry 120 performs logarithmic amplification, envelop detection processing, and the like on the reflected wave data received from the transceiving circuitry 110, to generate data (B-mode data) expressing a signal intensity at each sample point (observation point) by brightness. The B-mode processing circuitry 120 transmits the generated B-mode data to the image generating circuitry 140.

The Doppler processing circuitry 130 generates data (Doppler data) in which movement information of a moving body based on the Doppler effect is extracted at each sample point in a scanning region. Specifically, the Doppler processing circuitry 130 generates Doppler data in which an average speed, a dispersion value, a power value, and the like are extracted at each sample point as the movement information of a moving body. The moving body herein is, for example, a flow of blood, a tissue of a cardiac wall and the like, and a contrast agent. The Doppler processing circuitry 130 transmits the generated Doppler data to the image generating circuitry 140.

The image generating circuitry 140 generates ultrasonic image data from the data generated by the B-mode processing circuitry 120 or the Doppler processing circuitry 130. For example, the image generating circuitry 140 generates B-mode image data expressing an intensity of a reflected wave by brightness, from the B-mode data generated by the B-mode processing circuitry 120. Moreover, the image generating circuitry 140 generates Doppler image data expressing moving body information, from the Doppler data generated by the Doppler processing circuitry 130. This Doppler image data is speed image data, dispersion image data, power image data, or image data in which these are combined.

The image memory 150 is a memory that stores data generated by the B-mode processing circuitry 120, the Doppler processing circuitry 130, and the image generating circuitry 140. For example, the image memory 150 stores ultrasonic image data that is generated by the image generating circuitry 140, associating with an electrocardiographic wave of the subject P. When a data amount to be stored in the image memory 150 exceeds a storage capacity of the image memory 150, older data is deleted sequentially, to update the data.

The storage circuitry 160 is a storage device that stores various kinds of data. For example, the storage circuitry 160 stores a control program to perform transmission/reception of ultrasonic waves, image processing, and display processing, and various kinds of data such as diagnostic information (for example, patient ID, findings of a doctor, and the like), a diagnostic protocol, and various body marks. Moreover, the data stored in the storage circuitry 160 can be transferred to external devices through an interface not shown.

Furthermore, the storage circuitry 160 stores data that is generated by the B-mode processing circuitry 120, the Doppler processing circuitry 130, and the image generating circuitry 140. For example, the storage circuitry 160 stores ultrasonic image data corresponding to predetermined cardiac beats specified by an operator.

The communication control interface 180 controls communication with other devices through the network 50. For example, the communication control interface 180 is a network card or a network adaptor, and enables communication with other devices by being connected to the network 50 through an Ethernet (registered trademark) LAN. Moreover, for example, the communication control interface 180 enables wireless communication with other devices by being connected to the network 50 through a wireless LAN.

The processing circuitry 170 controls overall processing of the ultrasonic diagnostic device 100. Specifically, the processing circuitry 170 controls processing of the transceiving circuitry 110, the B-mode processing circuitry, the Doppler processing circuitry 130, the image generating circuitry 140, and the like based on various kinds of setting requests input by an operator through the input device 102, or various kinds of control programs and data that are read from the storage circuitry 160. Furthermore, the processing circuitry 170 causes the display 103 to display ultrasonic image data stored in the image memory 150.

Moreover, the processing circuitry 170 implements an acquiring function 171 and a setting-condition determining function 172 as shown in FIG. 8. Details of the acquiring function 171 and the setting-condition determining function 172 are described later.

Multiple components in FIG. 3 can be integrated into a single processor to implement the functions. The word "processor" used in the above explanation signifies a circuit, such as a CPU, a GPU, an ASIC, a programmable logic device (for example, SPLD), a CPULD, and an FPGA. The processor implements the function by reading and executing a program stored in the storage circuitry 160. The program can be directly installed in the circuit of the processor instead of storing the program in the storage circuitry 160. In this case, the processor implements the function by reading and executing the program installed in the circuit. Each processor in the present embodiment is not limited to be configured with a single circuit per processor, but can also be configured as a single processor by combining multiple independent circuits to implement the function.

Figure 9:
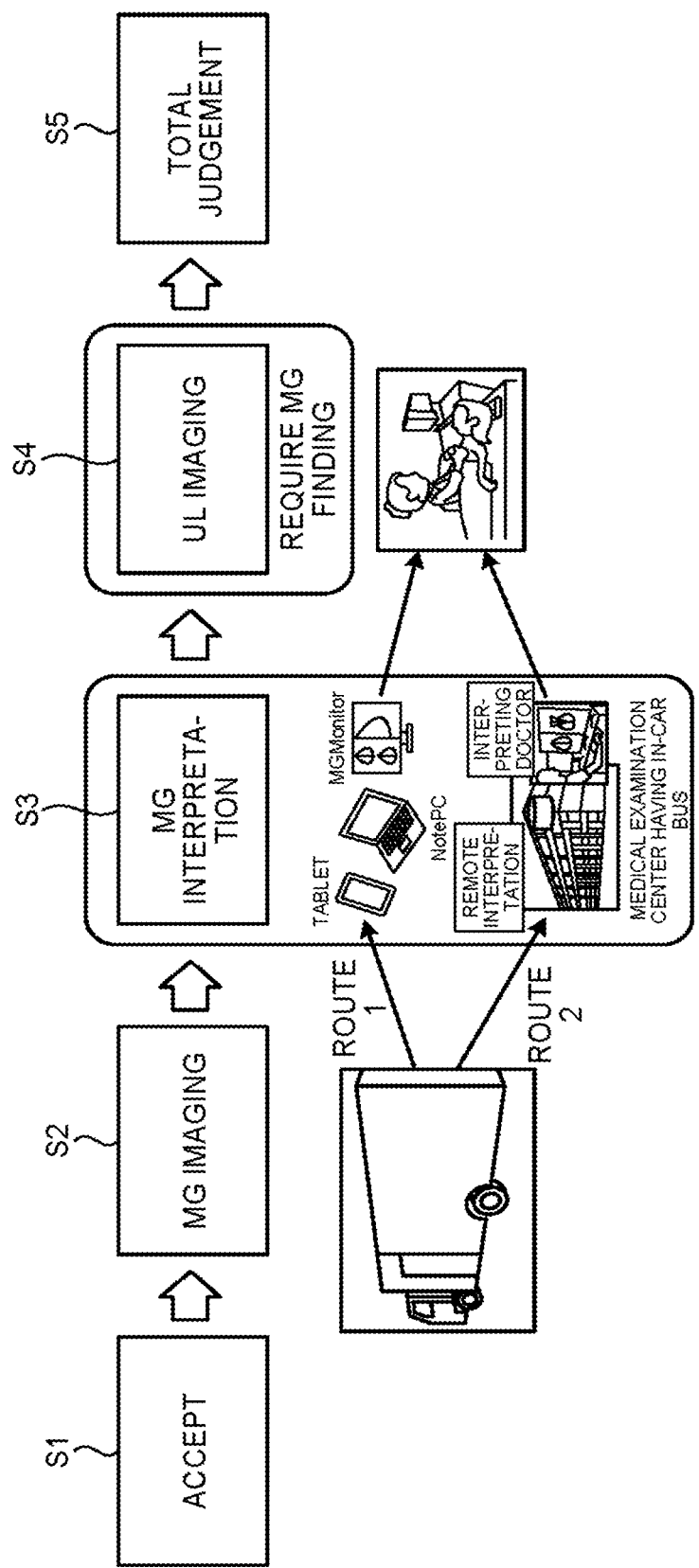
FIG. 9 depicts one example of mammographic diagnosis using both mammographic images and ultrasonic images.

In the medical information-processing system 1 as described, mammographic diagnosis using both a mammographic image and an ultrasonic image is conducted for a breast cancer examination. FIG. 9 depicts one example of mammographic diagnosis using both mammographic images and ultrasonic images.

As shown in FIG. 9, for example, the medical-insurance computing system of the in-hospital server device 10 accepts an appointment for a breast cancer examination (step S1). Subsequently, the mammography device 20 images a mammographic image (step S2). An interpreting doctor interprets the mammographic image step 3).

Subsequently, referring to a result of interpretation of the mammographic image, ultrasonic scanning is performed (step S4). The interpreting doctor then conducts mammography diagnosis using both mammographic images and ultrasonic images, and makes a total judgement (step S5).

In such an examination using both mammographic images and ultrasonic images, improvement in efficiency of workflow is desired. For example, a technique of automatically adjusting an image quality of an ultrasonic diagnostic device based on information of a quality of breast that has been obtained from a mammographic image, and a technique of identifying a position of a region of interest at the time of interpretation of a mammographic image to present it to an operator (sonographer) have been known.

When the ultrasonic scanning is performed at step S4, an operator (sonographer) of the ultrasonic diagnostic device 100 sets conditions of ultrasonographic diagnosis at the time of starting the ultrasonic scanning. For example, the sonographer operates the ultrasonic probe 101 with one hand, and operates the input device 102 with the ether hand, to set conditions of the ultrasonographic diagnosis. Moreover, the conditions of ultrasonographic diagnosis can vary according to a result of interpretation. Therefore, the sonographer is to set conditions of the ultrasonographic diagnosis per subject.

As described, the operation of setting conditions of ultrasonographic diagnosis at the time of starting ultrasonic scanning for each subject becomes a burden on the sonographer.

Figure 10:
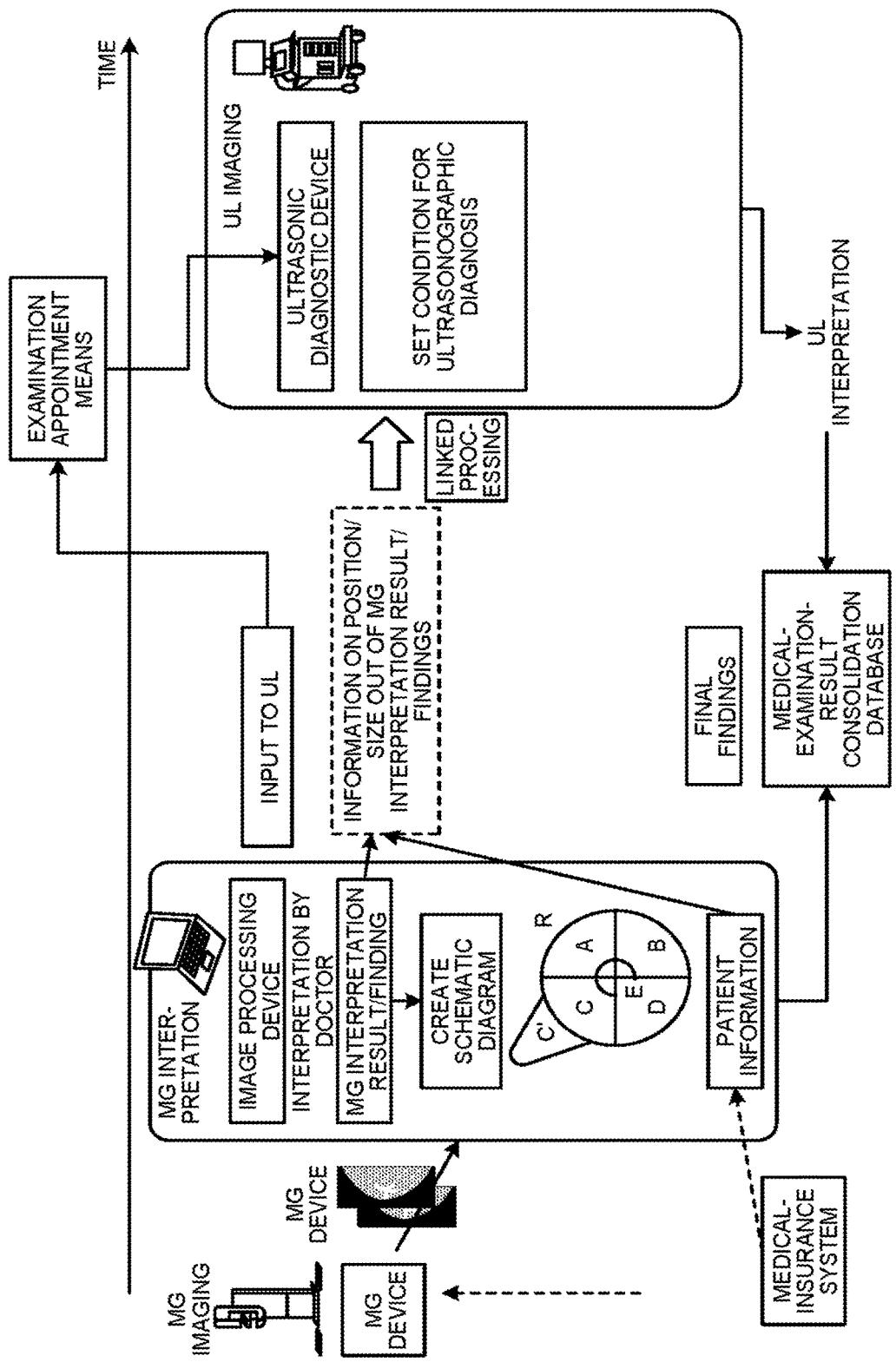
FIG. 10 is a diagram for explaining a flow of processing in the medical information-processing system according to the first embodiment.

Therefore, in the medical information-processing system 1, for example, region-of-interest information that indicates a position of a region of interest in a breast based on a result of interpretation of an X-ray image of the breast of a subject is acquired, and conditions of ultrasonographic diagnosis for the breast are set referring to the region-of-interest information at the time of starting ultrasonic scanning, thereby reducing the burden on the sonographer of the ultrasonic diagnostic device 100. The region of interest herein is, for example, an ROI set in a mammographic image, or a phyma on a mammographic image. Moreover, the region-of-interest information herein is the finding information 34b (for example, information about at least one of a position of a region of interest in a breast, a size of the region of interest, and a size of the breast), the schematic diagram to be archived, and the like. FIG. 10 is a diagram for explaining a flow of processing in the medical information-processing system 1 according to the first embodiment.

As shown in FIG. 10, for example, the medical-insurance computing system of the in-hospital server device 10 accepts an appointment for a breast cancer examination. Thus, the mammography device 2C images a mammographic image, and transmits the imaged mammographic image to the image processing device 30. The image processing device 30 generates finding information shown in FIG. 3 and FIG. 4 based on a result of interpretation by a doctor. Moreover, the image processing device generates a schematic diagram to be archived shown in FIG. 6 and FIG. 7.

The image processing device 30 transmits the result of interpretation of the mammographic image, and information relating to a position and a size out of the finding information 34b to the ultrasonic diagnostic device 100. That is, the ultrasonic diagnostic device 100 acquires the region-of-interest information that indicates a position of the region of interest in the breast based on the result interpretation of the mammographic image of the breast of the subject. The ultrasonic diagnostic device 100 then sets conditions of the ultrasonographic diagnosis of the breasts by referring to the region-of-interest information, at the time of starting ultrasonic scanning.

In the first embodiment, for example, a case of setting, at the time of starting ultrasonic scanning, a focus position in ultrasonic scanning as a transmission condition in the ultrasonographic diagnosis by the acquiring function 171 and the setting-condition determining function 172 implemented by the processing circuitry 170 of the ultrasonic diagnostic device 100 is explained.

The acquiring function 171 acquires information about at least one of a position of a region of interest in a breast, a size of the region of interest, and a size of the breast that is acquired based on an X-ray image of the breast of the subject, as the region-of-interest information. For example, the acquiring function 171 acquires information about at least one of a position of a region of interest in a breast, a size of the region of interest, and a size of the breast that is acquired based on a result of interpretation of an X-ray image of the breast of the subject, as the region-of-interest information. The acquiring function 171 acquires as the region-of-interest information, the "breast region information", the "distance from body surface to ROI", and the "size of phyma" that are stored as the finding information. For example, the acquiring function 171 acquires a distance to a region of interest from a body surface at the time of imaging an X-ray image as information on a position of the region of interest in the breast. Moreover, the acquiring function 171 acquires the region-of-interest information indicating the size of the region of interest. Furthermore, the acquiring function 171 acquires the region-of-interest information indicating the size of the breast.

The acquiring function 171 stores the acquired region-of-interest information in the storage circuitry 160. Thus, the storage circuitry 160 stores the region-of-interest information. That is, the storage circuitry 160 stores information about at least one of a position of a region of interest in a breast, a size of the region of interest, and a size of the breast that is acquired based on an X-ray image of the breast of the subject. For example, the storage circuitry 160 stores information about at least one of a position of a region of interest in a breast, a size of the region of interest, and a size of the breast that is acquired based on a result of interpretation of an X-ray image of the breast of the subject. In this example, the storage circuitry 160 stores the distance to the region of interest from the body surface at the time of imaging the X-ray image, as the information about a position of the region of interest in the breast.

The setting-condition determining function 172 sets a setting condition in ultrasonographic diagnosis of the breast by referring to the region-of-interest information. In other words, the setting-condition determining function 172 acquires a setting condition in the ultrasonographic diagnosis of a breast based on information about at least one of a position of a region of interest, a size of the region of interest, and a size of the breast. For example, the setting-condition determining function 172 refers to the distance to the region of interest from the body surface at the time of imaging an X-ray image, and acquires a transmission condition that a position according to the distance to the region of interest from the body surface on which the ultrasonic probe 101 to perform ultrasonic scanning abuts is a focus position in the ultrasonic scanning.

The setting-condition determining function 172 sets a focus position by using a coefficient that transforms the distance to the region of interest from the body surface in the mammographic image into a distance from the region of interest to the body surface in the ultrasonic image. In this example, it is explained assuming that the coefficient is 0.75. For example, when the finding information shown in FIG. 3 is acquired, the setting-condition determining function 172 sets the position to 3 centimeters (cm) because the "distance from body surface to ROI" is "4 cm". Moreover, for example, when the finding information shown in FIG. 4 is acquired, the setting-condition determining function 172 sets the focus position to 0.75 cm because the "distance from body surface to ROI" is "1 cm". The coefficient can be set arbitrarily. The coefficient for transforming the distance to a region of interest to a body surface in a mammographic image into a distance to a region of interest to a body surface in an ultrasonic image can be changed to any value according to an instruction of an operator.

Furthermore, the setting-condition determining function 172 arranges a mark that indicates the focus position in the ultrasonic scanning acquired as the setting condition or the ultrasonic image generated by the ultrasonic scanning, to display on the display 103 to be referred to at the time of ultrasonic scanning.

The acquiring function 171 and the setting-condition determining function 172 according to the first embodiment are explained using FIG. 11 to FIG. 14. FIG. 11 to FIG. 14 are diagrams for explaining the first embodiment. FIG. 11 shows an ultrasonic image that is displayed when the finding information shown in FIG. 3 is acquired, on the display 103 to be referred to at the time of ultrasonic scanning, and FIG. 12 shows an ultrasonic image that is displayed when the finding information shown in FIG. 4 is acquired, on the display 103 to be referred to at the time of ultrasonic scanning. As shown in FIG. 11, the setting-condition determining function 172 arranges "focus position 3 cm" and a triangular mark at a position corresponding to the focus position on the ultrasonic image. Moreover, as shown in FIG. 12, the setting-condition determining function 172 arranges "focus position 0.75 cm" and a triangular mark at a position corresponding to the focus position on the ultrasonic image.

Furthermore, the setting-condition determining function 172 sets a transmission condition that a display depth of the ultrasonic image that is generated by the ultrasonic scanning is a position according to the size of the breast. In other words, the setting-condition determining function 172 acquires a display depth of an ultrasonic image that is generated by the ultrasonic scanning at a position according to the size of a breast. The setting-condition determining function 172 sets a display scale by using display-scale setting information that defines criteria to set a display scale from the size of a breast. FIG. 13 depicts one example of the display-scale setting information.

As shown in FIG. 13, the display-scale setting information stores information in which "breast region information (size of breast)", "default setting", and "setting after change" are associated with each other. The "breast region information (size of breast)" indicates the size of a breast and, for example, "Large", "Middle", and "Small" are stored.

Moreover, the "default setting" indicates a default display depth and, for example, "8 cm" is stored. Moreover, the "setting after change" indicates a display depth according to the size of a breast and, for example, 10 cm", "not changed", and "5 cm" are stored.

As one example, when the finding information shown in FIG. 3 is acquired, the setting-condition determining function 172 sets a position of "10 cm" in a depth direction from the ultrasonic probe 101 to a display depth as shown in FIG. 11 because the "breast region information" is "L". Furthermore, when the finding information shown in FIG. 4 is acquired, the setting-condition determining function 172 sets a position of "5 cm" in the depth direction from the ultrasonic probe 101 to a display depth as shown in FIG. 12 because the "breast region information" is "3". Although ultrasonic images in different sizes are shown in FIG. 11 and FIG. 12 for the purpose of specifically showing the difference in the display depth, the region in which an ultrasonic image is displayed on the display 103 is uniform. Therefore, the processing circuitry 170 enlarges or reduces an ultrasonic image, for example, according to the display depth.

Furthermore, the setting-condition determining function 172 sets a condition for displaying an observation subject region according to a region of interest on an ultrasonic image that is generated by ultrasonic scanning on the display 103 to be referred to at the time of ultrasonic scanning. In other words, the setting-condition determining function 172 acquires a size of a mark that indicates an observation subject region according to a size of a region of interest as a setting condition, and arranges the mark indicating the observation subject region acquired as the setting condition on an ultrasonic image that is generated by ultrasonic scanning, to display on the display 103 to be referred to at the time of ultrasonic scanning. The setting-condition determining function 172 sets an ROI by using ROI setting information in which a criterion to set an ROI from a size of a phyma is defined. FIG. 14 depicts one example of the ROI setting information in which a criterion to set an ROI from a size of a phyma is defined.

As shown in FIG. 14, the ROI setting information stores information in which "size of phyma", "default setting", and "setting after change" are associated with each other. The "size of phyma" indicates a size of a phyma based on a result of interpretation and, for example, "5 millimeter (mm)", "2.5 mm", and "0.1 mm" are stored.

Furthermore, the "default settling" indicates a size of a default ROI and, for example, "5 mm" is stored. Moreover, the "setting after change" indicates a size of ROI according to a size of a phyma and, for example, "1 cm", "rot charged", and "0.2 mm" are stored.

As one example, when the finding information shown in FIG. 3 is acquired, the setting-condition determining function 172 sets the size of ROI to "1 cm" because the "size of phyma" is "5 cm" as shown in FIG. 11. Furthermore, when the finding information shown in FIG. 4 is acquired, the setting-condition determining function 172 sets the size of ROI to "5 mm" because the "size of phyma" is "2.5 mm" as shown in FIG. 12. Moreover, the setting-condition determining function 172 can be enabled to change the shape of ROI according to a shape of a phyma.

FIG. 15 is a flowchart of a processing procedure of the ultrasonic diagnostic device 100 according to the first embodiment. As shown in FIG. 15, the acquiring function 171 acquires the region-of-interest information based on a result of interpretation from the mammography device 20 (step S101).

Subsequently, the region-of-interest information setting-condition determining function 172 sets the display scale (display depth) based on the size of a breast (step S102). Subsequently, the setting-condition determining function 172 sets a focus based on a distance to an ROI from a body surface (step S103). Furthermore, the setting-condition determining function 172 sets an ROI width based on the size of a phyma (step S104). After the setting processing by the setting-condition determining function 172, the processing circuitry 170 controls ultrasonic scanning by the ultrasonic probe 101, to start imaging an ultrasonic image (step S105). Note that it can be configured such that only one of the step S102, the step S103, and the step S104 shown in FIG. 15 is performed, or that one is not performed. Furthermore, the processing sequence of the step S102, the step S103, and the step S104 can be arbitrarily changed.

As described above, in the first embodiment, a distance to a region of interest, such as a phyma, from a body surface at the time of imaging a mammographic image is acquired as region-of-interest information. The region-of-interest information is referred to at the time of ultrasonographic diagnosis, to set a transmission condition that a distance according to the distance to the region of interest from the body surface on which the ultrasonic probe 101 to perform ultrasonic scanning abuts is a focus position. Thus, according to the first embodiment, for example, a burden on the sonographer can be reduced.

Moreover, in the first embodiment, a mark indicating a focus position in ultrasonic scanning is further arranged on an ultrasonic image that is generated by ultrasonic scanning, to be displayed on the display 103 referred to at the time of ultrasonic scanning. Thus, according to the first embodiment, for example, a sonographer can easily find a region of interest, such as a phyma, by referring to the mark of the focus position to grasp the focus position visually. As a result, according to the first embodiment, a burden on the sonographer can be reduced.

Furthermore, in the first embodiment, region-of-interest information that indicates the size of a region of interest is acquired, and a display condition that an observation subject region according to the size of the region of interest is displayed on an ultrasonic image that is generated by ultrasonic scanning on the display 103 that is referred to at the time of ultrasonic scanning is further set. Thus, according to the first embodiment, for example, a sonographer can visually grasp the size of a region of interest to be an examination subject in advance, to perform ultrasonic scanning. As a result, according to the first embodiment, for example, a burden on the sonographer can be reduced.

Furthermore, in the first embodiment, a transmission condition that a position according to the size of a breast is a display depth of an ultrasonic image that is generated by ultrasonic scanning is set. Thus, according to the first embodiment, for example, since a scanning range according to the size of the breast is specified, a sonographer can examine the specified scanning range carefully. As a result, according to the first embodiment, for example, a burden on the sonographer can be reduced.

As described, in the first embodiment, at the time of starting ultrasonic scanning, a transmission condition such as a focus position and a display depth is set as an initial condition. Furthermore, in the first embodiment, a focus position or an ROI is displayed on the display 103. Thus, according to the first embodiment, a burden on the sonographer can be reduced. As a result, according to the first embodiment, time required for ultrasonic scanning can be shortened, to improve the workflow.

Second Embodiment

In the first embodiment, a case of setting a focus position in ultrasonic scanning as a transmission condition has been explained. A sonographer arranges a probe mark at a position on a body mark that corresponds to an imaging region before starting ultrasonic scanning of each imaging region.

For example, when a right breast is to be imaged, a sonographer displays a body mark for a right breast on the display 103. The sonographer then positions a schematic ultrasonic probe at a position on the body mark corresponding to the imaging region in the right breast. Subsequently, the sonographer starts imaging and acquires an ultrasonic image.

When the imaged ultrasonic image is to be saved, the body mark in which the ultrasonic probe is arranged at a position on the body mark corresponding to the imaging region is stored, associating with the ultrasonic image. On the other hand, when an imaging region is shifted to continue imaging without saving the imaged ultrasonic image, a probe mark is arranged at a position on a body mark that corresponds to the imaging region after the shift, and then imaging is started. Thus, an interpreting doctor can grasp which region has been imaged to obtain the imaged ultrasonic image.

Moreover, a sonographer sometimes refers to a result of interpretation of a mammographic image to perform ultrasonic scanning. For example, referring to the schematic diagrams to be archived shown in FIG. 6 and FIG. 7, ultrasonic scanning is performed by abutting the ultrasonic probe 101 at a position on a patient corresponding to a position of a phyma in the schematic diagram to be archived. In such a case, the sonographer is to perform an operation of placing a probe mark at a position on a body mark corresponding to an imaging region before starting ultrasonic scanning of each imaging region. The operation of thus arranging a probe mark at a position on a body mark corresponding to an imaging region before starting ultrasonic scanning can be a burden on a sonographer.

Therefore, in a second embodiment, a case in which information that indicates a position on which the ultrasonic probe 101 abuts is arranged on a schematic diagram (body mark) for ultrasonic scanning at the time of starting ultrasonic scanning, for example, by the acquiring function 171 and the setting-condition determining function 172 implemented by the processing circuitry 170 of the ultrasonic diagnostic device 100 to conduct ultrasonographic diagnosis is explained.

A configuration example of a medical information-processing system according to the second embodiment is similar to the configuration example shown in FIG. 1, except a part of functions that are executed by the acquiring function 171 and the setting-condition determining function 172 of the processing circuitry 170 included in the ultrasonic diagnostic device 100. The acquiring function 171 and the setting-condition determining function 172 according to the second embodiment are explained by using FIG. 16 to FIG. 19. FIG. 16 to FIG. 19 are diagrams for explaining the second embodiment.

The acquiring function 171 acquires region-of-interest information that indicates a position of a region of interest in a breast based on an X-ray image of the breast of a subject. For example, the acquiring function 171 acquires region-of-interest information that indicates a position of a region of interest in the breast based on a result of interpretation of the X-ray image of the breast of the subject. The acquiring function 171 according to the second embodiment acquires information about a position of a region of interest on a schematic diagram for breast diagnosis that schematically expresses a breast acquired based on a result of interpretation of an X-ray image of the breast of the subject as the region-of-interest information. For example, the acquiring function 171 acquires the schematic diagram to be archived shown in FIG. 6 or the schematic diagram to be archived shown in FIG. 7, as the region-of-interest information.

The acquiring function 171 then stores the acquired region-of-interest information in the storage circuitry 160. Thus, the storage circuitry 160 stores the region-of-interest information. That is, the storage circuitry 160 stores information about a position of a region of interest on a schematic diagram for breast diagnosis schematically expressing a breast acquired based on an X-ray image of the breast of a subject. For example, the storage circuitry 160 stores information about a position of a region of interest on a schematic diagram for breast diagnosis schematically expressing a breast acquired based on a result of interpretation of an X-ray image of a breast of a subject.

The setting-condition determining function 172 arranges a condition in ultrasonographic diagnosis of a breast, referring to the region-of-interest information. The setting-condition determining function 172 according to the second embodiment refers to the region-of-interest information at the time of starting ultrasonic scanning, arranges information that indicates a position on which the ultrasonic probe 101 abuts on a schematic diagram for ultrasonic scanning, to set a display condition to be displayed on the display 103 that is referred to at the time of ultrasonic scanning.

Figures 16, 17:
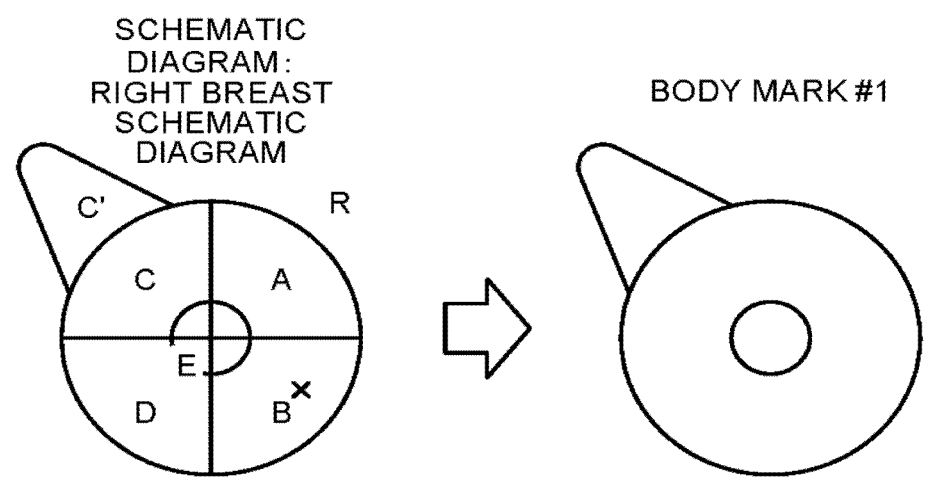
FIG. 16 is a diagram (1) for explaining a second embodiment.
FIG. 17 is a diagram (2) for explaining the second embodiment.

For example, by using correspondence information in which a schematic diagram for mammographic diagnosis and a body mark for ultrasonic diagnosis are associated with each other, the setting-condition determining function 172 selects an appropriate body mark from the schematic diagram. FIG. 16 depicts one example of the correspondence information in which a schematic diagram for mammographic diagnosis and body mark for ultrasonic scanning are associated with each other. As shown in FIG. 16, a right breast schematic diagram for mammographic diagnosis is associated with a body mark #1 for ultrasonic diagnosis, and a left breast schematic diagram for mammographic diagnosis is associated with a body mark #2 for ultrasonic diagnosis.

The setting-condition determining function 172 selects the body mark #1 for ultrasonic diagnosis when the right breast schematic diagram is acquired, and selects the body mark #2 for ultrasonic diagnosis when the left breast schematic diagram is acquired. In FIG. 17, the body mark #1 that is selected by the setting-condition determining function 172 when the right breast schematic diagram is acquired is shown.

Figure 18:
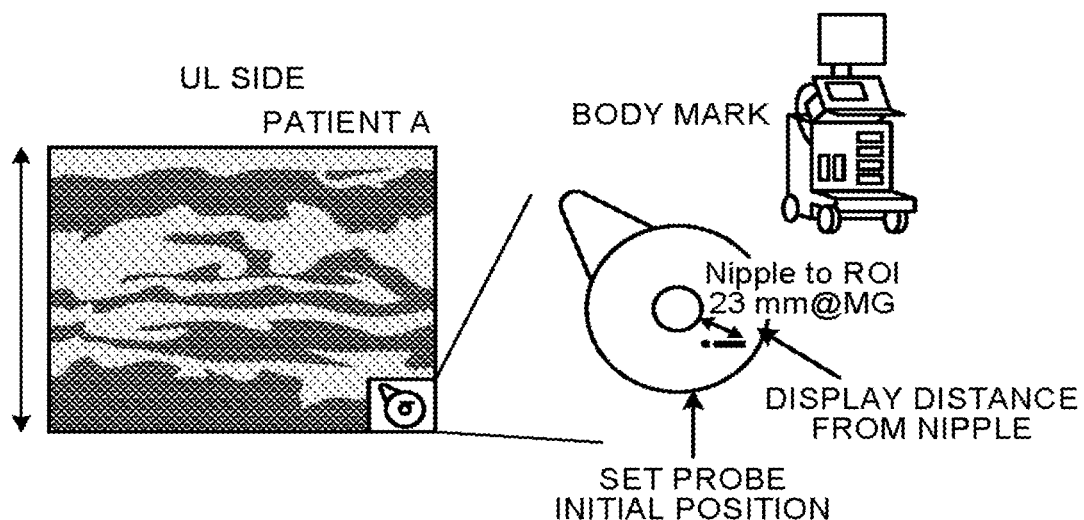
FIG. 18 is a diagram (3) for explaining the second embodiment.

Subsequently, the setting-condition determining function 172 sets an initial probe position from the schematic diagram. When the schematic diagram shown in FIG. 6 is acquired, the setting-condition determining function 172 determines a position of a region of interest is the region B of the right breast. The setting-condition determining function 172 then arranges a probe mark that indicates an initial position of the probe at a position corresponding to a region of interest positioned in the region B of the right breast in the body mark #1 for ultrasonic diagnosis as shown in FIG. 18.

Figure 19:
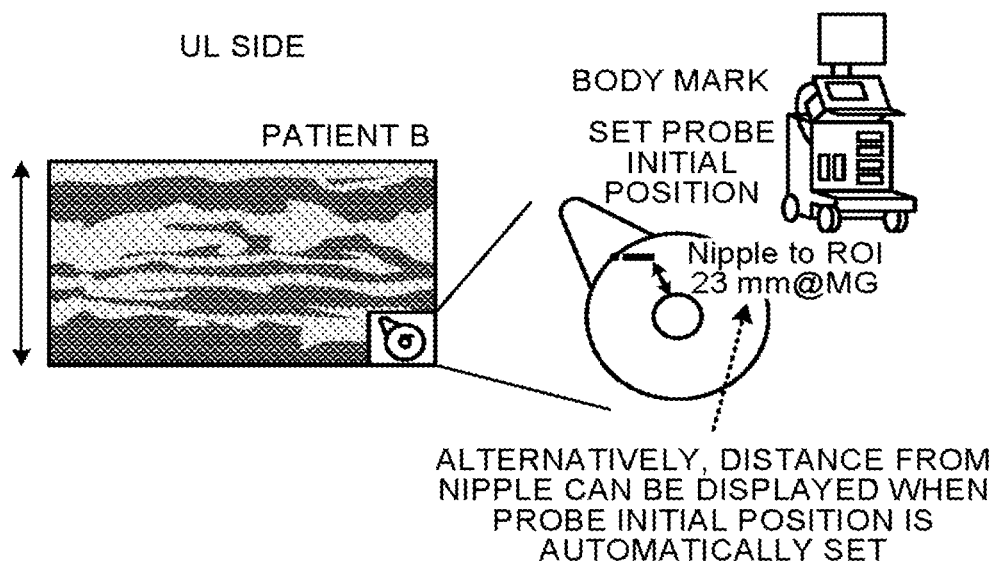
FIG. 19 is a diagram (4) for explaining the second embodiment.

Furthermore, when the schematic diagram shown in FIG. 7 is acquired, the setting-condition determining function 172 determines that a position of a region of interest is the region C of the right breast. The setting-condition determining function 172 then arranges a probe mark that indicates an initial position of the probe at a position corresponding to a region of interest positioned in the region C of the right breast in the body mark 41 for ultrasonic diagnosis as shown in FIG. 19. The position of the probe mark arranged by the setting-condition determining function 172 is not required to be an accurate position, and can be an approximate position corresponding to a region of interest in a schematic diagram to be archived. As described, the setting-condition determining function 172 refers to information of a position of a region of interest at the time of starting ultrasonic scanning, to acquire a position at which information that indicates a position on which the ultrasonic probe 101 abuts is arranged on a schematic diagram for ultrasonic scanning, as setting condition in ultrasonographic diagnosis. Subsequently, the setting-condition determining function 172 displays the schematic diagram for ultrasonic scanning in which the information that indicates the position on which the ultrasonic probe 101 abuts is arranged at the acquired position, on the display 103 to be referred at the time of ultrasonic scanning.

Moreover, the setting-condition determining function 172 refers to the finding information 34b, and further arranges information that indicates a distance between a position on which the ultrasonic probe 101 abuts and a nipple on the schematic diagram for ultrasonic scanning. For example, the setting-condition determining function 172 sets "Nipple to ROI 23 mm@MG" and a double pointed arrow on the body mark as the information that indicates a distance between a position on which the ultrasonic probe abuts and a nipple as shown in FIG. 18. Furthermore, the setting-condition determining function 172 "Nipple to ROI 23 mm@MG" and a double pointed arrow on the body mark as the information that indicates a distance between a position on which the ultrasonic probe 101 abuts and a nipple as shown in FIG. 19. Note that the information that indicates a distance between a position on which the ultrasonic probe abuts and a nipple is not limited to the example shown in FIG. 18. For example, the information that indicates a distance between a position on which the ultrasonic probe abuts and a nipple can be changed arbitrarily as long as it indicates a distance from a nipple in a mammographic image.

Figure 20:
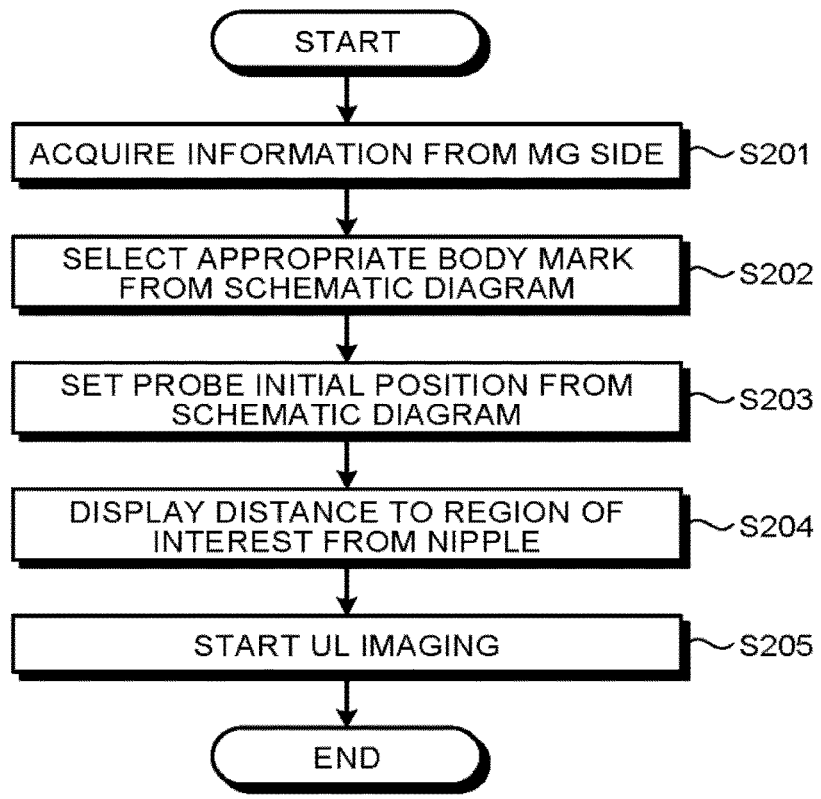
FIG. 20 is a flowchart of a processing procedure of an ultrasonic diagnostic device according to the second embodiment.

FIG. 20 is a flowchart of a processing procedure of the ultrasonic diagnostic device 100 according to the second embodiment. As shown in FIG. 20, the acquiring function 171 acquires region-of-interest information based on a result interpretation from the mammography device 20 (step S201).

Subsequently, the setting-condition determining function 172 selects an appropriate body mark from a schematic diagram (step S202). The setting-condition determining function 172 then sets a probe initial position from the schematic diagram (step S203). Subsequently, the setting-condition determining function 172 displays a distance to a region of interest from a nipple (step S204). After the setting processing by the setting-condition determining function 172 is completed, the processing circuitry 170 controls ultrasonic scanning by the ultrasonic probe 101 and starts imaging an ultrasonic image (step S205).

As described above, the ultrasonic diagnostic device 100 according to the second embodiment acquires a position of a region of interest on a schematic diagram for breast diagnosis schematically expressing a breast, as region-of-interest information. The ultrasonic diagnostic device 100 according to the second embodiment refers to the region-of-interest information at the time of starting ultrasonic scanning, and arranges information that indicates a position on which the ultrasonic probe 101 abuts on a schematic diagram for ultrasonic scanning, thereby setting a display condition to be displayed on the display 103 that is referred to at the time of ultrasonic scanning. Thus, according to the second embodiment, a sonographer can omit an operation of arranging a schematic ultrasonic probe manually at a position on a body mark corresponding to an imaging region at the time of starting ultrasonic scanning. Furthermore, the sonographer can grasp an approximate scanning position visually at the time of starting the examination. As a result, according to the second embodiment, for example, a burden on a sonographer can be reduced, and time required for an ultrasonic examination can be shortened to improve the workflow.

Third Embodiment

A sonographer performs scanning, for example, in scanning order that has been set by default in an ultrasonic examination. The sonographer can scan a region of interest, such as a lesion, giving a priority thereto, when ultrasonic scanning is performed by referring to a schematic diagram to be archived. Therefore, in a third embodiment, a case in which scanning order for plural regions in a breast in ultrasonic scanning is set, as a scanning condition, by referring to the region-of-interest information by the acquiring function 171 and the setting-condition determining function 172 executed by the processing circuitry 170 of the ultrasonic diagnostic device 100, for example, at the time of starting ultrasonic scanning is explained.

Note that a configuration example of a medical information-processing system according to the third embodiment is similar to the configuration example shown in FIG. 1 except a part of function that is executed by the acquiring function 171 and the setting-condition determining function 172 of the processing circuitry 170 included in the ultrasonic diagnostic device 100.

The acquiring function 171 acquires region-of-interest information that indicates a position of a region of interest in a breast based on an X-ray image of the breast of a subject. For example, the acquiring function 171 acquires region-of-interest information that indicates a position of a region of interest in a breast based on a result of interpretation of an X-ray image of the breast of a subject. The acquiring function 171 according to the third embodiment acquires information about a position of a region of interest on a schematic diagram for breast diagnosis schematically expressing a breast acquired based on a result of interpretation of an X-ray image of the breast of a subject as region-of-interest information. For example, the acquiring function 171 acquires the schematic diagram to be archived shown in FIG. 6 or the schematic diagram to be archived shown in FIG. 7 as the region-of-interest information.

The acquiring function 171 stores the acquired region-of-interest information in the storage circuitry 160. Thus, the storage circuitry 160 stores the region-of-interest information. That is, the storage circuitry 160 stores information about a position a region of interest on a schematic diagram for breast diagnosis schematically expressing a breast acquired based on an X-ray image of a breast of a subject. For example, the storage circuitry 160 stores information about a position of a region of interest on a schematic diagram for breast diagnosis schematically expressing a breast of a subject acquired based on a result of interpretation of an X-ray image of the breast of a subject.

The setting-condition determining function 172 sets a condition in ultrasonographic diagnosis for a breast by referring to the region-of-interest information. The setting-condition determining function 172 according to the third embodiment refers to information about a position of a region of interest and acquires scanning order for plural regions of the breast in ultrasonic scanning as a setting condition in ultrasonographic diagnosis of a breast.

Figure 21:
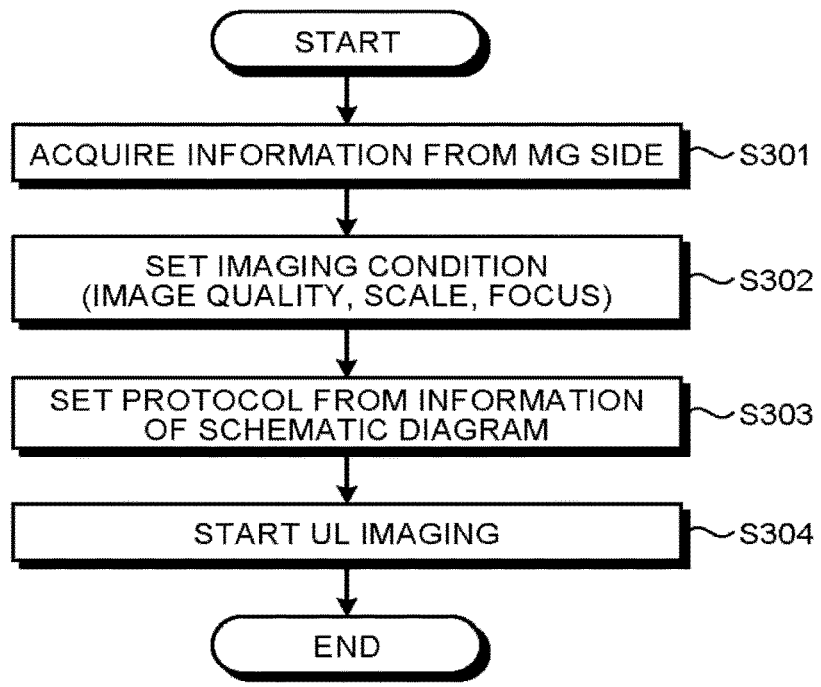
FIG. 21 is a flowchart of a processing procedure of an ultrasonic diagnostic device according to a third embodiment.

FIG. 21 is a flowchart of a processing procedure of the ultrasonic diagnostic device 100 according to a third embodiment. As shown in FIG. 21, the acquiring function 171 acquires region-of-interest information based on a result of interpretation from the mammography device 20 (step S301). For example, the acquiring function 171 acquires a "schematic diagram to be archive" as the region-of-interest information.

Subsequently, the processing circuitry 170 sets an imaging condition (step S302). For example, the processing circuitry 170 sets an image quality, a display scale (display depth), and a focus position. The processing circuitry 170 can set a display scale (display depth) or a focus position similarly to the first embodiment.

Moreover, the setting-condition determining function 172 sets a protocol from information of the schematic diagram (step S303). Details of step S303 are described later using FIG. 22 to FIG. 24. After completion of the setting processing by the setting-condition determining function 172, the processing circuitry 170 controls ultrasonic scanning by the ultrasonic probe 101, and starts imaging of an ultrasonic image (step S304).

Figure 22:
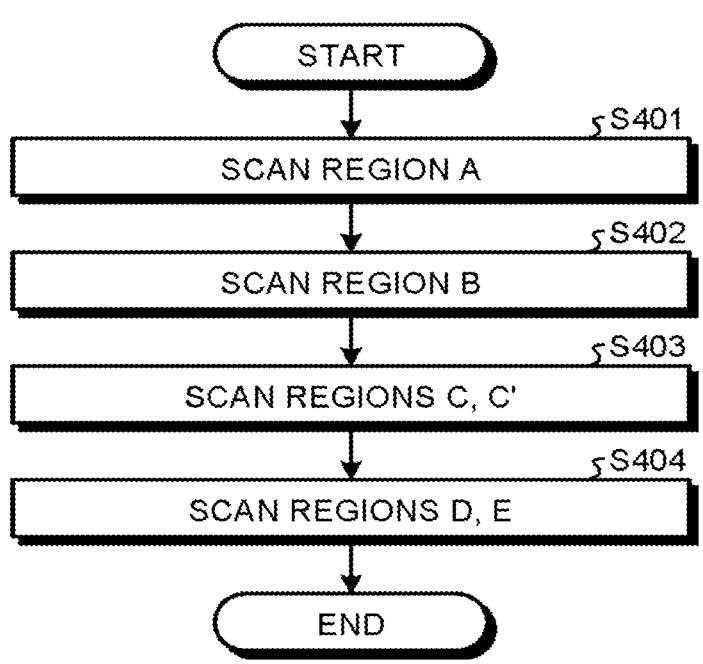
FIG. 22 is a diagram (1) for explaining the third embodiment.
Figure 23:
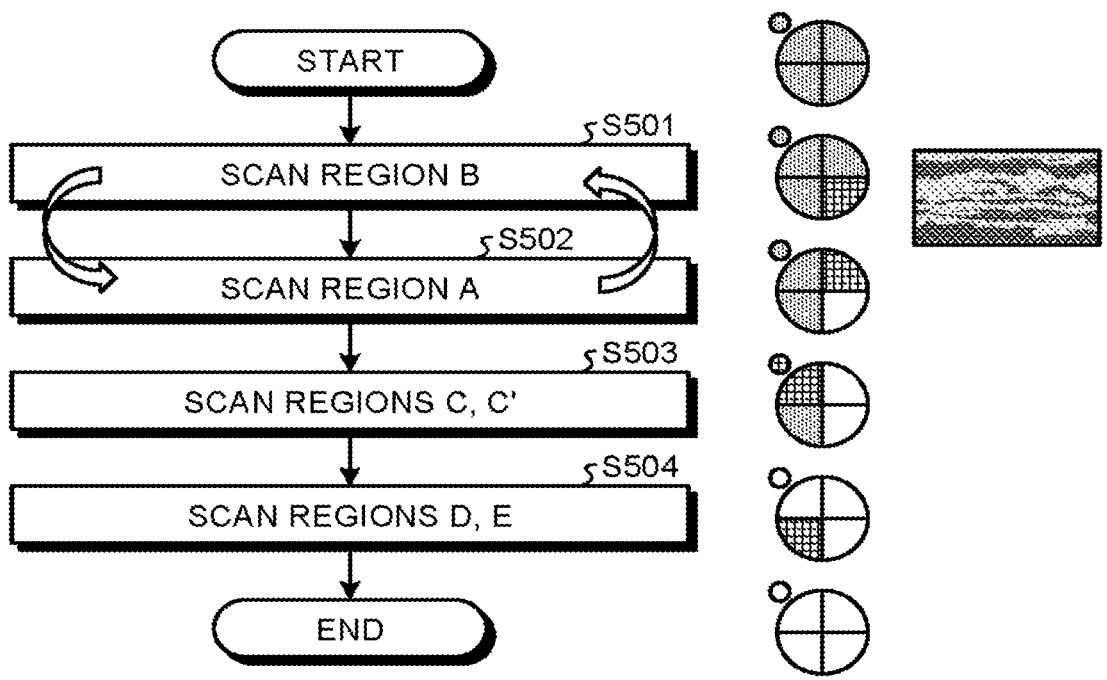
FIG. 23 is a diagram for explaining the third embodiment.
Figure 24:
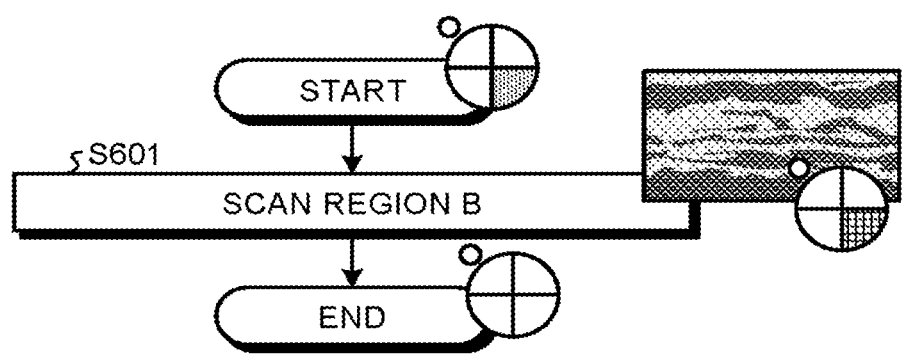
FIG. 24 is a diagram (3) for explaining the third embodiment.

FIG. 22 to FIG. 24 are diagrams for explaining the third embodiment. In FIG. 22, processing when a region of interest is not included in a schematic diagram to be archived is explained. In such a case, the setting-condition determining function 172 sets scanning order that has been set by default, as a scanning condition. In the scanning order that has been set by default, a sonographer scans the region A of a breast as shown in a right drawing in FIG. 22 (step S401), and subsequently scans the region step S402). The sonographer then scans the regions C, C' (step S403), and finally scans the regions D, E (step S404). Note that the scanning order set by default explained in FIG. 22 is only one example, and different scanning order may be set by default depending on a scanner or a facility.

Furthermore, the setting-condition determining function 172 displays scanning order indicating a region before scanning, a region being scanned, and a region after scanning in respective different forms on the display 103 that is referred to at the time of ultrasonic scanning. For example, the setting-condition determining function 172 divides a body mark for ultrasonic scanning into four, the region A, the region B, the regions C and C', and the regions D and E, and shows a region before scanning with dots, the region being scanned in shades, and shows the region after scanning in white, as shown in a right drawing in FIG. 22.

The setting-condition determining function 172 shows the entire region in the body mark with dots indicating it is before scanning, as shown in the right drawing in FIG. 22, at the time of start. Subsequently, the setting-condition determining function 172 shows the region A that is scanned first in shades indicating that it is being scanned at step S401, and shows the rest of the regions, the region B, the regions C and C', and the regions D and E in dots indicating that it is before scanning.

The setting-condition determining function 172 then shows the region B to be scanned next in shades indicating that it is being scanned at step S402 after completion of scanning of the region A, and shows the rest of the regions, the regions C and C' and the regions D and E with dots indicating that it is before scanning.

Furthermore, the setting-condition determining function 172 shows the regions C and C' to be scanned next in shades indicating that it is being scanned at step S403 after completion of scanning of the region B, and shows the region A and the region B subjected to scanning in white, and shows the remaining regions D and E with dots indicating that it is before scanning. Subsequently, the setting-condition determining function 172 shows the regions D and E to be scanned next in shades indicating that it is being scanned after completion of scanning of the regions C and C' at step S404, and shows the region A, the region B, and the regions C and C' subjected to scanning in white. The setting-condition determining function 172 then shows the entire region in white indicating that scanning is finished, after completion of scanning of the regions D and E.

In the example shown in FIG. 22, processing when a region of interest is not included in the schematic diagram to be archived has been explained. On the other hand, when a region of interest is included in the schematic diagram to be archived, a region including the region of interest can be given a priority to be scanned, not following the scanning order set by default. Therefore, a case in which the setting-condition determining function 172 gives a higher priority in scanning order to a region that corresponds to information of a position of a region of interest out of plural regions in a breast is explained by using FIG. 23.

In the example shown in FIG. 23, it is assumed that a region of interest is included in the region B in the schematic diagram to be archived as shown in FIG. 6. In such a case, the setting-condition determining function 172 gives a high priority in scanning order to the region B as shown in the right drawing in FIG. 23, in the scanning order set by default shown in FIG. 22. That is, in the scanning order in which a high priority is given to the region B in scanning order, as shown in the right drawing in FIG. 23, the sonographer scans the region B of the breast (step S501), and then scans the region A (step S502). The sonographer then scans the regions C and C' (step S503), and finally scans the regions D and E (step S504).

The setting-condition determining function 172 displays a region before scanning, a region being scanned, and a region after scanning in respective different forms on the display 103 that is referred to at the time of ultrasonic scanning as shown in the right drawing in FIG. 23, also in the case of giving a high priority in scanning order to a region that corresponds to region-of-interest information.

In the example shown in FIG. 23, a case of giving a priority to a region including a region of interest to be scanned has been explained. However, the setting-condition determining function 172 can be configured to set only a region that corresponds to information of a position of a region of interest to a scanning region in ultrasonic scanning, out of plural regions in a breast. In an example shown in FIG. 24, a case in which a region of interest is included in the region B in the schematic diagram to be archived is explained. In such a case, the setting-condition determining function 172 scans the region B (step S601), and ends the processing. Moreover, the setting-condition determining function 172 displays, as shown in the right drawing in FIG. 24, a region before scanning, a region being scanned, and a region after scanning in respective different forms on the display 103 that is referred to at the time of ultrasonic scanning. In such a case, the setting-condition determining function 172 shows only the region B with dots indicating that it is before scanning, and shows the other regions A, C and C', and D and E in white indicating that it is after scanning. The setting-condition determining function 172 then shows the region B to be scanned first in shades indicating that it is being scanned at step S601, and shows the remaining regions A, C and C', and D and E in white indicating that it is after scanning. After completion of scanning of the region B, the setting-condition determining function 172 shows all of the regions in white indicating that it is after scanning.

As described, in the third embodiment, a position of region of interest on a schematic diagram for breast diagnosis schematically expressing a breast is acquired as region-of-interest information, and the region-of-interest information is referred to at the time of ultrasonographic diagnosis, to set scanning order for plural regions of a breast in ultrasonic scanning as a scanning condition. Thus, according to the third embodiment, for example, a sonographer can examine a region of interest suspected to be a lesion first, giving a priority thereto. Furthermore, a sonographer can grasp scanning order visually at the time of starting an examination. As a result, according to the third embodiment, for example a burden on a sonographer can be reduced, and time required for an ultrasonic examination can be shortened to improve the workflow.

Although it has been explained, in the third embodiment, that scanning order is set by referring to a position of a region of interest based on a result of interpretation of a mammographic image, embodiments are not limited thereto. For example, there is a case that a blind area that is a region that cannot be imaged in mammographic imaging is present among regions of a breast. Considering such a problem, the ultrasonic diagnostic device 100 according to the third embodiment can be configured to set scanning order by referring to a position of a blind area.

Figure 25:
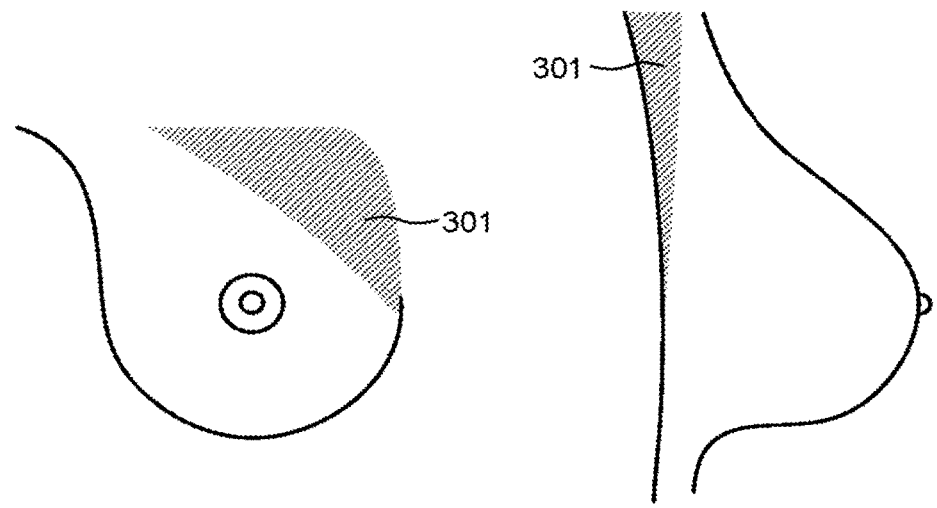
FIG. 25 depicts a blind area in imaging a mediolateral oblique (MLO) image.
Figure 26:
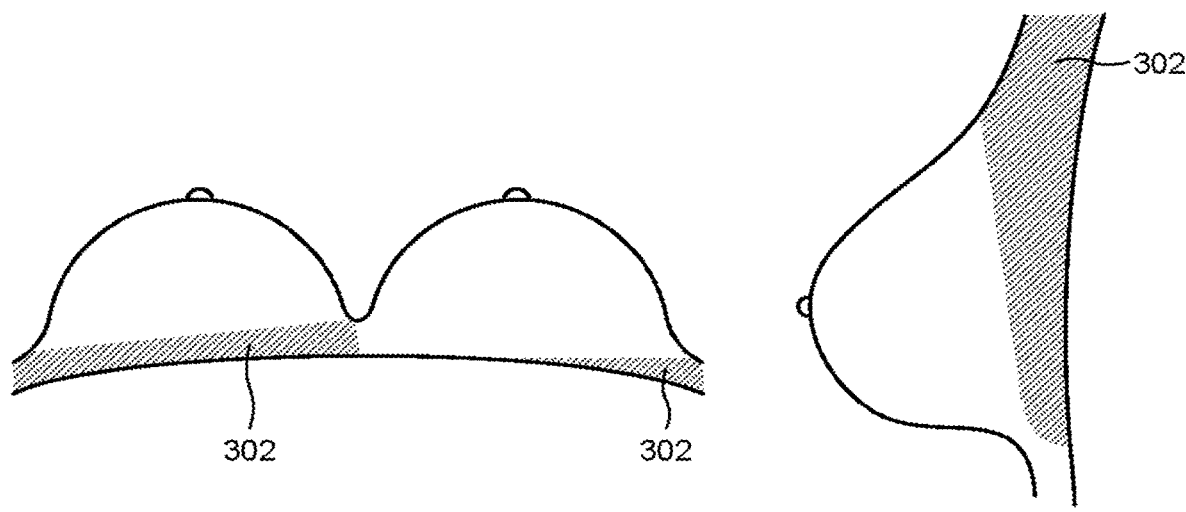
FIG. 26 depicts a blind area in imaging a craniocaudal (CC) image.

FIG. 25 depicts a blind area in imaging an MLO image, and FIG. 26 depicts a blind area in imaging a CC image. For example, as shown in FIG. 25, in imaging of an MLO image, blind areas 301 tend to be produced at an upper inner side (refer to a left drawing in FIG. 25) and a lower portion (refer to a right drawing in FIG. 25) of a breast. Moreover, for example, as shown in FIG. 26, in imaging of a CC image, blind areas 302 tend to be produced at an upper portion (refer to a left drawing in FIG. 26) and a side close to an outer armpit (refer to a right drawing in FIG. 26).

For example, when a lesion is included in a blind area produced in imaging of an MLO image or imaging of a CC image, there is a case in which a region of interest is not set in at least one of the MLO image and the CC image. For example, as shown in the left drawing in FIG. 25, when a lesion is present in the blind area on the upper inner side of the breast, it is possible that the lesion is not shown in the MLO image, and as a result, a region of interest is not set in the MLO image. Furthermore, for example, as shown in the left drawing in FIG. 26, when a lesion is present in the blind area in an upper portion of the breast, it is possible that the lesion is not shown in the CC image, and as a result, a region of interest is not set in the CC image.

Considering such a problem, for example, when a region of interest is not set in at least one of an MLO image and a CC image, information indicating a blind area can be displayed on a schematic diagram of a breast. In such a case, for example, in the image processing device 30, the position specifying function 35e further identifies whether a blind area is produced based on a mammographic image. The position specifying function 35e then generates a schematic diagram to be archived that indicates position information of a blind area on the schematic diagram, in addition to position information of a region of interest on the schematic diagram, based on a result of identification. Subsequently, for example, the ultrasonic diagnostic device 100 further outputs the position information of the blind area on the schematic diagram together with the position information of the region of interest on the schematic diagram, based on the schematic diagram to be archived that is generated by the position specifying function 35e.

Referring to the schematic diagram to be archived, and when determining that a blind area is produced, the setting-condition determining function 172 can give a priority in order of scanning to a region in which the blind area is produced.

Moreover, the setting-condition determining function 172 can be configured to automatically specify an application to be used at the time of imaging by the ultrasonic diagnostic device 100 based on a finding of a mammographic image. For example, when calcification is found from information of a region of interest set in a mammographic image, the setting-condition determining function 172 applies a protocol that an application of facilitating observation of calcified condition starts easily. Moreover, for example, for a phyma that is difficult to be identified whether it is benign or malignant, the setting-condition determining function 172 applies a protocol that enables to easily image a color Doppler image from which information on blood flow can be acquired, or an elastography image from which information on hardness of the phyma can be acquired.

Another Embodiment

Embodiments are not limited to the embodiments described above.

For example, although it has been explained, in the above embodiments, that region-of-interest information (position of a region of interest in a breast, size of the region of interest, size of a breast, and position of a region of interest on a schematic diagram for breast diagnosis schematically expressing a breast) is acquired based on a result of interpretation of an X-ray image of a breast of a subject made by a doctor, such as an interpreting doctor, embodiments are not limited thereto. For example, the acquiring function 171 can acquire region-of-interest information based on information that is added by a technician that refers to an X-ray image. For example, a technician refers to an X-ray image, and stores "breast region information (size of breast)", "distance from body surface to ROI", and "size/shape of phyma" associating with each other in the storage circuitry 34. Alternatively, a technician refers to an X-ray image, and generates a schematic diagram to be archived, adding a mark at a position of a region of interest on a schematic diagram for breast diagnosis schematically expressing a breast. The technician then stores the generated schematic diagram to be archived in the storage circuitry 34, associating with a patient ID that is assigned to a subject of examination. That is, the acquiring function 171 acquires region-of-interest information (information about at least one of a position of a region of interest in a breast, a size of the region of interest, a size of the breast, and a position of a region of interest on a schematic diagram for breast diagnosis schematically expressing the breast) that is acquired based on an X-ray image of the breast of the subject. The acquiring function 171 then stores the acquired region-of-interest information in the storage circuitry 160. Thus, the storage circuitry 160 stores the region-of-interest information (information about at least one of a position of the region of interest in the breast, the size of the region of interest, the size of the breast, and the position of the region of interest on the schematic diagram for breast diagnosis schematically expressing the breast) that is acquired based on the X-ray image of the breast of the subject.

There is a case that a mammographic image is read again after imaging by the ultrasonic diagnostic device 100, referring to a result of interpretation of an ultrasonic image. Considering such a case, it can be controlled to display mammographic images in optimal order at the time of reading the mammographic image, by transmitting position information of a region of interest that is set based on a result of interpretation of an ultrasonic image that is imaged by the ultrasonic diagnostic device 100 to the image processing device 30.

In such a case, the processing circuitry of the ultrasonic diagnostic device 100 further executes a position specifying function. The position specifying function identifies position information of a region of interest that is set in an ultrasonic image. The position specifying function then transmits the identified position information of the region of interest to the image processing device 30. The processing circuitry 35 of the image processing device 30 further executes an image reading function. The image reading function switches between an MLO image and a CC image determining which is prioritized to be displayed, based on the position information of the region of interest identified by the position specifying function. Thus, in a total judgement phase, the workflow of interpreting mammographic images can be optimized by linking to a result of interpretation of an ultrasonic image.

Although it has been explained, in the above embodiment, that the acquiring function 171 and the setting-condition determining function 172 are executed in the ultrasonic diagnostic device 100, embodiments are not limited thereto. For example, it can be configured to execute the acquiring function 171 and the setting-condition determining function 172 in the image processing device 30. Alternatively, it can be configured to execute the acquiring function 171 in the image processing device 30, and the setting-condition determining function 172 in the ultrasonic diagnostic device 100.

In the explanation of the embodiments described above, the illustrated respective components of the respective devices are of functional concepts, and it is not necessarily required to be configured physically as illustrated. That is, a specific form of distribution and integration of the respective devices is not limited to the one illustrated, but all or a part thereof can be configured be distributed or integrated functionally or physically in arbitrary units according to various kinds of loads, a use condition, and the like. Furthermore, as for the respective functions executed in the respective devices, all or a part thereof can be implemented by a CPU and a program that is analyzed and executed by the CPU, or can be implemented as hardware by wired logic.

Moreover, the control method explained in the above embodiments can be implemented by executing a control program that is prepared in advance by a computer, such as a personal computer and a workstation. This control program can be distributed through a network such as the Internet. Furthermore, this control program can be stored in a computer-readable recording medium, such as a hard disk, an FD, a CD-ROM, an MO, and a DVD, and can be executed by being read from the recording medium by a computer.

According to at least one of the embodiment explained above, the workflow can be improved in efficiency in an examination using both mammographic images and ultrasonic images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image-processing apparatus comprising:
   storage circuitry configured to store information about at least one of a position of a region of interest in a breast, a size of the region of interest, and a size of the breast, the information acquired based on an X-ray image of a breast of a subject; and
   setting-condition determining circuitry configured to:
   set at least one setting condition of an ultrasonic diagnostic device used in ultrasonographic diagnosis for the breast, according to the information about at least one of the position of the region of interest, the size of the region of interest, and the size of the breast, and
   acquire a display depth of an ultrasonic image, that is to be generated by ultrasonic scanning at a position, according to a size of the breast, as a setting condition.

2. The medical image-processing apparatus according to claim 1, wherein
   the storage circuitry stores a distance to the region of interest from a body surface at the time of imaging the X-ray image, as the information of the position of the region of interest in the breast, and
   the setting-condition determining circuitry refers to the distance to the region of interest from the body surface at the time of imaging the X-ray image, and acquires a transmission condition that a position according to the distance to the region of interest from the body surface on which an ultrasonic probe to perform ultrasonic scanning abuts is a focus position in the ultrasonic scanning, as a setting condition.

3. The medical image-processing apparatus according to claim 2, wherein
   the setting-condition determining circuitry arranges, on an ultrasonic image that is generated by the ultrasonic scanning, a mark that indicates a focus position in the ultrasonic scanning acquired as the setting condition, to display on a display that is to be referred to at the time of ultrasonic scanning.

4. The medical image-processing apparatus according to claim 1, wherein
   the setting-condition determining circuitry acquires a size of a mark that indicates an observation subject region according to the size of the region of interest as a setting condition, and arranges the mark that indicates the observation subject region acquired as the setting condition on an ultrasonic image generated by ultrasonic scanning, to display on a display that is to be referred to at the time of the ultrasonic scanning.

5. The medical image-processing apparatus according to claim 1, wherein
   the storage circuitry further stores information of a position of a region of interest on a schematic diagram for breast diagnosis, based on an X-ray image of a breast of a subject, the schematic diagram schematically expressing the breast, and
   the setting-condition determining circuitry acquires scanning order in ultrasonic scanning for a plurality of regions in the breast by referring to the information of the position of the region of interest, as a setting condition.

6. The medical image-processing apparatus according to claim 5, wherein
   the setting-condition determining circuitry sets only a region that corresponds to the information on the position of the region of interest to a scanning region in the ultrasonic scanning, out of a plurality of regions in the breast.

7. The medical image-processing apparatus according to claim 5, wherein
   the setting-condition determining circuitry gives a priority in the scanning order to a region that corresponds to the information on the position of the region of interest, out of a plurality of regions in the breast.

8. The medical image-processing apparatus according to claim 5, wherein
   the setting-condition determining circuitry displays scanning order that is expressed with a region before scanning, a region being scanned, and a region after scanning in respective different forms, on a display that is to be referred to at the time of the ultrasonic scanning.

9. A medical image-processing apparatus comprising:
   storage circuitry configured to store information on a position of a region of interest in a schematic diagram for breast diagnosis acquired based on an X-ray image of a breast of a subject, the schematic diagram schematically expressing the breast; and
   setting-condition determining circuitry configured to:
   select, at the time of starting ultrasonic scanning, a schematic diagram corresponding to the schematic diagram for the breast diagnosis from a plurality of schematic diagrams for ultrasonic scanning,
   acquire a position at which information indicating a position on which an ultrasonic probe abuts is arranged on the selected schematic diagram for ultrasonic scanning by referring to the information on a position of the region of interest, display the selected schematic diagram for ultrasonic scanning on which the information indicating the position on which the ultrasonic probe abuts is arranged at the acquired position, on a display that is to be referred to at the time of the ultrasonic scanning, and display, on the selected schematic diagram, information indicating a distance between an initial position for the ultrasonic probe and a nipple of the breast.

10. The medical image-processing apparatus according to claim 9, wherein the setting-condition determining circuitry further arranges information that indicates a distance between the position at which the ultrasonic probe abuts and a nipple on the schematic diagram for the ultrasonic scanning.

11. The medical image-processing apparatus according to claim 9, wherein the setting-condition determining circuitry acquires scanning order in ultrasonic scanning for a plurality of regions in the breast by referring to the information of the position of the region of interest.

12. The medical image-processing apparatus according to claim 11, wherein the setting-condition determining circuitry sets only a region that corresponds to the information on the position of the region of interest to a scanning region in the ultrasonic scanning, out of a plurality of regions in the breast.

13. The medical image-processing apparatus according to claim 11, wherein the setting-condition determining circuitry gives a priority in the scanning order to a region that corresponds to the information on the position of the region of interest, out of a plurality of regions in the breast.

14. The medical image-processing apparatus according to claim 11, wherein the setting-condition determining circuitry displays scanning order that is expressed with a region before scanning, a region being scanned, and a region after scanning in respective different forms, on a display that is to be referred to at the time of the ultrasonic scanning.

15. An ultrasonic diagnostic device comprising:

storage circuitry configured to store information about at least one of a position of a region of interest in a breast, a size of the region of interest, and a size of the breast, the information acquired based on an X-ray image of a breast of a subject; and setting-condition determining circuitry configured to:

set at least one setting condition of the ultrasonic diagnostic device used in ultrasonographic diagnosis for the breast, according to the information about at least one of the position of the region of interest, the size of the region of interest, and the size of the breast, and acquire a display depth of an ultrasonic image that is to be generated by ultrasonic scanning at a position, according to a size of the breast, as a setting condition.

16. An ultrasonic diagnostic device comprising:

storage circuitry configured to store information on a position of a region of interest in a schematic diagram for breast diagnosis acquired based on an X-ray image of a breast of a subject, the schematic diagram schematically expressing the breast; and setting-condition determining circuitry configured to:

select, at the time of starting ultrasonic scanning, a schematic diagram corresponding to the schematic diagram for the breast diagnosis from a plurality of schematic diagrams for ultrasonic scanning, acquire a position at which information indicating a position on which an ultrasonic probe abuts is arranged on the selected schematic diagram for ultrasonic scanning by referring to the information on a position of the region of interest, display the selected schematic diagram for ultrasonic scanning on which the information indicating the position on which the ultrasonic probe abuts is arranged at the acquired position, on a display that is to be referred to at the time of the ultrasonic scanning, and display, on the selected schematic diagram, information indicating a distance between an initial position for the ultrasonic probe and a nipple of the breast.

\* \* \* \* \*